United States Patent
Harada et al.

(10) Patent No.: US 8,624,266 B2
(45) Date of Patent: Jan. 7, 2014

(54) SILICON CARBIDE SUBSTRATE, SEMICONDUCTOR DEVICE, METHOD OF MANUFACTURING SILICON CARBIDE SUBSTRATE AND METHOD OF MANUFACTURING SEMICONDUCTOR DEVICE

(75) Inventors: Shin Harada, Osaka (JP); Tsubasa Honke, Itami (JP)

(73) Assignee: Sumitomo Electric Industries, Ltd., Osaka-shi, Osaka (JP)

( * ) Notice: Subject to any disclaimer, the term of this patent is extended or adjusted under 35 U.S.C. 154(b) by 200 days.

(21) Appl. No.: 13/334,855

(22) Filed: Dec. 22, 2011

(65) Prior Publication Data
US 2012/0161155 A1 Jun. 28, 2012

Related U.S. Application Data
(60) Provisional application No. 61/427,308, filed on Dec. 27, 2010.

(30) Foreign Application Priority Data
Dec. 27, 2010 (JP) .................. 2010-289593

(51) Int. Cl.
*H01L 29/24* (2006.01)
*C30B 23/04* (2006.01)

(52) U.S. Cl.
USPC ........... 257/77; 257/89; 257/94; 257/103; 257/E21.09; 257/E21.53; 257/E29.104; 438/16; 438/430; 438/503; 438/589; 117/84; 117/106; 117/109

(58) Field of Classification Search
USPC ........... 257/77, 89, 94, 103, E21.09, E21.53, 257/E29.104; 438/16, 430, 503, 589; 117/84, 106, 109
See application file for complete search history.

(56) References Cited

U.S. PATENT DOCUMENTS

| 7,314,520 B2 | 1/2008 | Powell et al. |
| 2003/0080345 A1* | 5/2003 | Motoki et al. ............. 257/103 |

(Continued)

FOREIGN PATENT DOCUMENTS

| JP | 2005-154247 | 6/2005 |
| JP | 2006-321707 | 11/2006 |

(Continued)

OTHER PUBLICATIONS

M. Nakamura et al., "Effects of Excitation Power and Temperature on Photoluminescence from Stacking Faults in 4H—SiC Epilayers", Japanese Journal of Applied Physics, Jan. 25, 2010, vol. 49, No. 1, pp. 010202-1-010202-3.

(Continued)

*Primary Examiner* — Dao H Nguyen
(74) *Attorney, Agent, or Firm* — Drinker Biddle & Reath LLP

(57) ABSTRACT

A main surface of a silicon carbide substrate is inclined by an off angle in an off direction from {0001} plane of a hexagonal crystal. The main surface has such a characteristic that, among emitting regions emitting photoluminescent light having a wavelength exceeding 650 nm of the main surface caused by excitation light having higher energy than bandgap of the hexagonal silicon carbide, the number of those having a dimension of at most 15 μm in a direction perpendicular to the off direction and a dimension in a direction parallel to the off direction not larger than a value obtained by dividing penetration length of the excitation light in the hexagonal silicon carbide by a tangent of the off angle is at most $1 \times 10^4$ per 1 $cm^2$. Accordingly, reverse leakage current can be reduced.

17 Claims, 21 Drawing Sheets

(56) References Cited

U.S. PATENT DOCUMENTS

2008/0202409 A1* 8/2008 Motoki et al. ............... 117/84
2009/0302326 A1* 12/2009 Maruyama .................. 257/77
2011/0206929 A1  8/2011 Nakabayashi et al.
2012/0112320 A1* 5/2012 Kubo et al. ............... 257/615

FOREIGN PATENT DOCUMENTS

| | | |
|---|---|---|
| JP | 2007-230823 | 9/2007 |
| JP | 2008-515749 | 5/2008 |
| JP | 2009-256138 | 11/2009 |
| JP | 2010-95397 | 4/2010 |
| WO | WO 2006/041660 | 4/2006 |

OTHER PUBLICATIONS

M. Tajima et al., "Nondestructive Characterization of Dislocations and Micropipes in High-Resistivity 6H—SiC Wafers by Deep-Level Photoluminescence Mapping", Applied Physics Letters, 2005, vol. 86, No. 6, pp. 061914-1-061914-3.

H. Tsuchida, "SiC Crystal Growth and Characterization", Central Research Institute of Electric Power Industry, vol. EFM-06, No. 25-35, 2006, pp. 43-48, with English abstract.

T. Mitani, "[Special Edition] Semiconductor, (7) Assessment of SiC Crystal Defect", TRC News, 2008, No. 104, pp. 37-38, with English comment.

* cited by examiner

SILICON CARBIDE SUBSTRATE, SEMICONDUCTOR DEVICE, METHOD OF MANUFACTURING SILICON CARBIDE SUBSTRATE AND METHOD OF MANUFACTURING SEMICONDUCTOR DEVICE

BACKGROUND OF THE INVENTION

1. Field of the Invention

The present invention relates to a silicon carbide substrate, a semiconductor device, a method of manufacturing a silicon carbide substrate, and a method of manufacturing a semiconductor device.

2. Description of the Background Art

Recently, a silicon carbide substrate has come to be used for manufacturing semiconductor devices as disclosed, for example, in U.S. Pat. No. 7,314,520 (Patent Literature 1). As compared with silicon as a more widely used material, silicon carbide has wider band-gap. Therefore, a semiconductor device using a silicon carbide substrate has advantages such as high breakdown voltage and low on-resistance and, in addition, its property does not much degrade in high-temperature environment.

SUMMARY OF THE INVENTION

In some semiconductor devices, a forward direction in which current should flow and a reverse direction in which current should not flow are defined. Here, it is desired that the current flowing in the reverse direction, or reverse leakage current, should be as small as possible. If a semiconductor device is manufactured using a silicon carbide substrate, however, the reverse leakage current tends to be large.

Therefore, an object of the present invention is to provide a silicon carbide substrate and a semiconductor device enabling reduction of reverse leakage current.

The silicon carbide substrate in accordance with the present invention, having a side surface and a main surface surrounded by the side surface, has a hexagonal crystal structure. The main surface is inclined by an off angle in an off direction from {0001} plane of the hexagonal crystal. The main surface has such a characteristic that, among the regions emitting photoluminescent light having a wavelength exceeding 650 nm of the main surface caused by excitation light having higher energy than band-gap of the hexagonal silicon carbide, the number of those having a dimension of at most 15 μm in a direction perpendicular to the off direction and a dimension in a direction parallel to the off direction not larger than a value obtained by dividing penetration length of the excitation light in the hexagonal silicon carbide by a tangent of the off angle is at most $1\times10^4$ per 1 cm².

In the silicon carbide substrate, the emitting region may be a region emitting photoluminescent light having a wavelength exceeding 750 nm, or the emitting region may be a region emitting photoluminescent light having a wavelength exceeding 650 nm and shorter than 950 nm, or the emitting region may be a region emitting photoluminescent light having a wavelength exceeding 750 nm and shorter than 950 nm.

Preferably, the main surface has such a characteristic that the number of the emitting regions is at most $1\times10^4$ per 1 cm².

The silicon carbide substrate may include a silicon carbide layer having the main surface, and a base substrate supporting the silicon carbide layer. The silicon carbide layer is epitaxially formed on the base substrate.

The semiconductor device in accordance with the present invention has the above-described silicon carbide substrate.

The method of manufacturing a silicon carbide substrate in accordance with the present invention includes the following steps. A plurality of silicon carbide single crystals each having a main surface and a crystal structure of hexagonal crystal are prepared. Photoluminescence of the main surface of each of the plurality of silicon carbide single crystals is measured. The step of measuring photoluminescence includes the step of irradiating the main surface with excitation light having higher energy than band-gap of the hexagonal silicon carbide, and the step of observing emitting regions of photoluminescent light having a wavelength exceeding 650 nm caused by the excitation light. Crystal growth of silicon carbide is attained through sublimation method, using as a seed crystal one of the plurality of silicon carbide single crystals of which number of the emitting regions per unit area is smaller than a prescribed number.

In the method of manufacturing a silicon carbide substrate described above, the emitting region may be a region emitting photoluminescent light having a wavelength exceeding 750 nm, or the emitting region may be a region emitting photoluminescent light having a wavelength exceeding 650 nm and shorter than 950 nm, or the emitting region may be a region emitting photoluminescent light having a wavelength exceeding 750 nm and shorter than 950 nm.

The method of manufacturing a semiconductor device in accordance with the present invention includes the following steps. A plurality of silicon carbide substrates each having a main surface and a crystal structure of hexagonal crystal are prepared. Photoluminescence of the main surface of each of the plurality of silicon carbide substrates is measured. The step of measuring photoluminescence includes the step of irradiating the main surface with excitation light having higher energy than band-gap of the hexagonal silicon carbide, and the step of observing emitting regions of photoluminescent light having a wavelength exceeding 650 nm caused by the excitation light. A defective region having the number of emitting regions per unit area on the main surface larger than a prescribed number is removed from a product fabricating region as a region for fabricating the semiconductor device.

In the method of manufacturing a semiconductor device described above, the emitting region may be a region emitting photoluminescent light having a wavelength exceeding 750 nm, or the emitting region may be a region emitting photoluminescent light having a wavelength exceeding 650 nm and shorter than 950 nm, or the emitting region may be a region emitting photoluminescent light having a wavelength exceeding 750 nm and shorter than 950 nm.

The step of removing may include the step of removing the silicon carbide substrate having the defective region from manufacturing process of the semiconductor device.

The step of removing may include the step of removing the defective region of the silicon carbide substrate having the defective region from manufacturing process of the semiconductor device, and determining a region other than the defective region as the product fabricating region.

By the present invention, the reverse leakage current in the semiconductor device having a silicon carbide substrate can be reduced.

The foregoing and other objects, features, aspects and advantages of the present invention will become more apparent from the following detailed description of the present invention when taken in conjunction with the accompanying drawings.

DESCRIPTION OF THE PREFERRED EMBODIMENTS

In the following, embodiments of the present invention will be described with reference to the figures.

Embodiment 1

Figure 1:
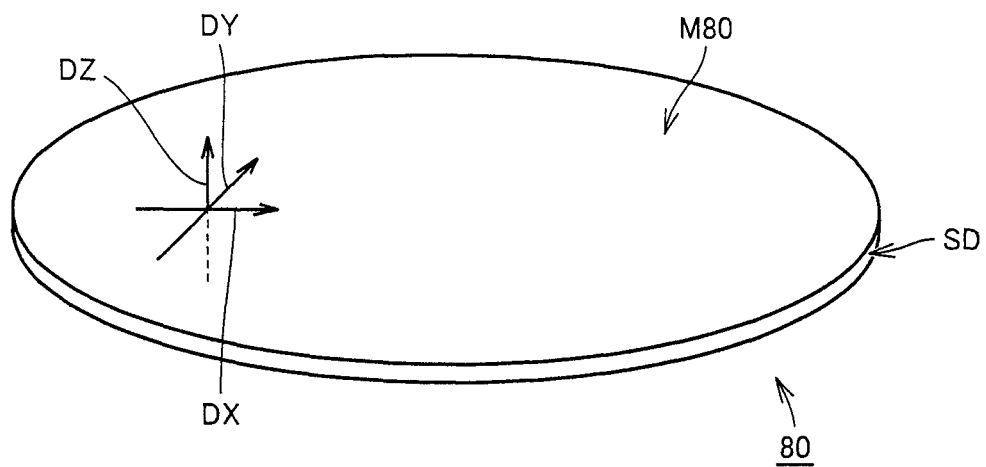
FIG. 1 is a perspective view schematically showing a structure of a silicon carbide substrate in accordance with Embodiment 1 of the present invention.

As shown in FIG. 1, a silicon carbide substrate in accordance with the present invention is a single crystal substrate 80 (silicon carbide substrate) formed of silicon carbide having hexagonal crystal structure. Single crystal substrate 80 has a side surface SD and a main surface M80 surrounded by the side surface SD. Polytype of the hexagonal crystal is, preferably, 4H.

Figure 2:
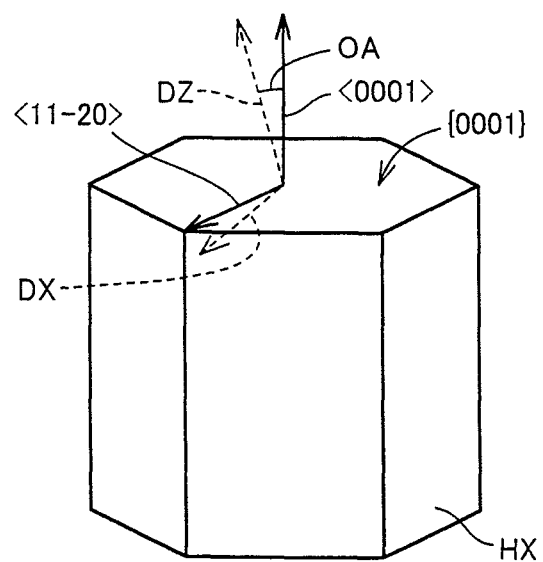
FIG. 2 is a perspective view showing the crystal structure, with off angle and off direction, of silicon carbide substrate of FIG. 1.

Further, as shown in FIG. 2, main surface M80 (FIG. 1) is tilted by an off angle OA relative to {0001} plane of the hexagonal crystal HX. Specifically, normal direction DZ of main surface M80 is inclined by off angle OA from <0001> direction. The tilting is in off direction DX. In the figure, a direction DY represents a direction perpendicular to the direction DX. In the present embodiment, the off direction DX corresponds to <11-20> direction on the {0001} plane.

Main surface M80 of single crystal substrate 80 has specific photoluminescence characteristics as will be described later. Measurement of photoluminescence and an apparatus used for measurement will be described in the following.

Figure 3:
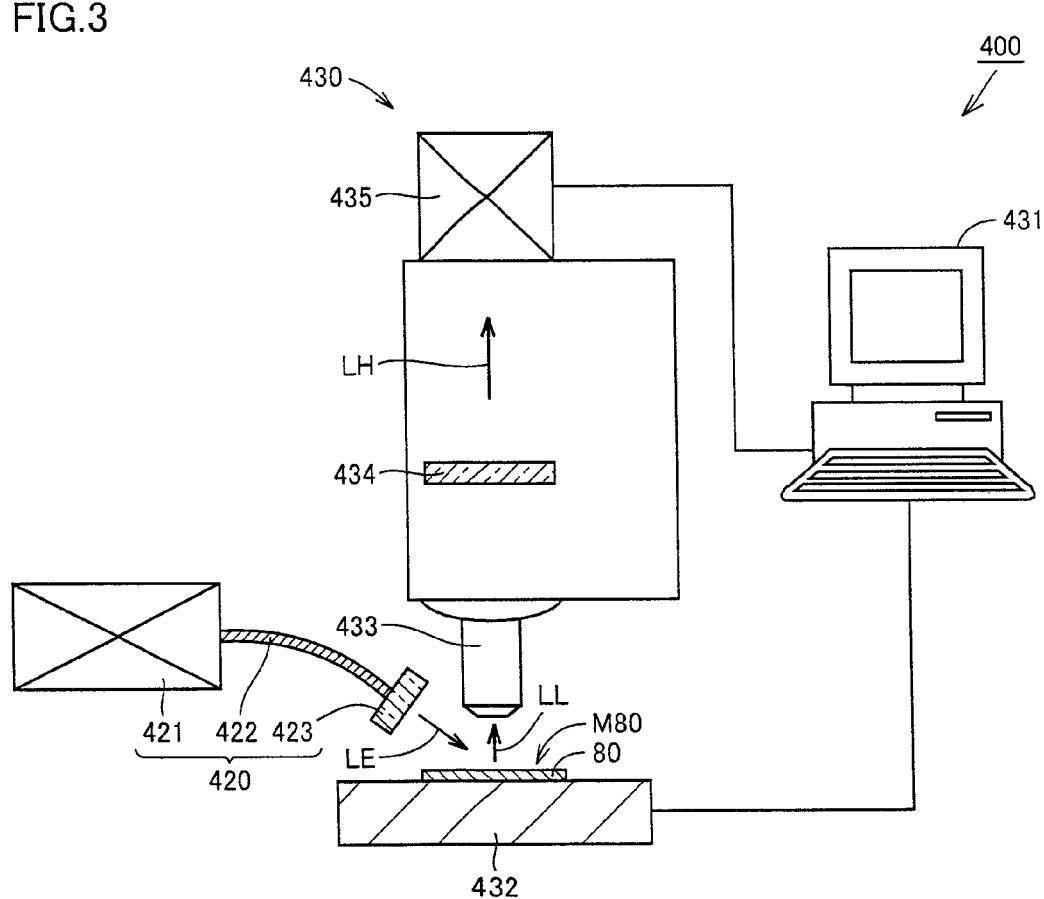
FIG. 3 is a block diagram schematically showing a configuration of a measuring apparatus used for photoluminescence measurement of the silicon carbide substrate shown in FIG. 1.

As shown in FIG. 3, a photoluminescence measuring apparatus 400 has an excitation light generating unit 420 and a microscope unit 430.

Excitation light generating unit 420 has a light source section 421, a light guiding section 422 and a filter 423. Light source section 421 is a light source involving energy component higher than band-gap of hexagonal crystal silicon carbide and, by way of example, it is a mercury lamp. Light guiding section 422 guides the light emitted from light source section 421 and, by way of example, it includes an optical fiber. Filter 423 is for selectively passing light having a specific wavelength corresponding to the energy higher than the band-gap of hexagonal crystal silicon carbide. The wavelength corresponding to the band-gap of hexagonal crystal silicon carbide is typically about 390 nm. Therefore, a band-pass filter that particularly passes light having the wavelength of about 313 nm, for example, may be used as filter 423. By this configuration, excitation light generating unit 420 can emit excitation light LE having higher energy than the bandgap of hexagonal crystal silicon carbide.

Microscope unit 430 has a control section 431, a stage 432, an optical system 433, a filter 434 and a camera 435. Control section 431 controls an operation of changing position of stage 432 and controls an operation of image pick-up by camera 435 and, by way of example, it is implemented by a personal computer. Stage 432 is for supporting single crystal substrate 80 to have main surface M80 exposed and for changing position of main surface M80 and, by way of example, it is an X-Y stage. Optical system 433 is for receiving photoluminescent light LL emitted from main surface M80 excited by excitation light LE. Camera 435 is for picking-up an image formed by transmitted light LH that has passed through filter 434 and for transmitting the data to control section 431 and, by way of example, it is a CCD camera.

Filter 434 selectively passes light having a wavelength exceeding 650 nm, of the light received by optical system 433. Here, "selectively passes light having a wavelength exceeding 650 nm" means that it substantially does not pass light in the wavelength range of 650 nm or shorter, and passes light in at least a part of the wavelength range exceeding 650 nm. Filter 434 may be a filter that selectively passes light having a wavelength longer than a prescribed wavelength. Alternatively, filter 434 may be a band-pass filter. Filter 434 may be one that selectively passes a wavelength exceeding 750 nm, or filter 434 may be one that selectively passes a wavelength exceeding 650 nm and shorter than 950 nm. Here, "selectively passes a wavelength exceeding 650 nm and shorter than 950 nm" means that it substantially does not pass light in the wavelength ranges of 650 nm or shorter and 950 nm or longer, and passes light in at least part of the wavelength range exceeding 650 nm and shorter than 950 nm. Filter 434 may be one that passes a wavelength exceeding 750 nm and shorter than 950 nm.

Next, how to use photoluminescence measuring apparatus 400 will be described.

Main surface M80 of single crystal substrate 80 is irradiated with excitation light LE. Consequently, emission of photoluminescent light LL occurs on main surface M80. Transmitted light LH, which is photoluminescent light LL passed through filter 434, is observed as an image by camera 435. Specifically, on main surface M80, photoluminescent light LL having a wavelength longer than 650 nm is observed. Which range of the wavelength exceeding 650 nm is observed is determined by characteristics of filter 434.

Figure 4:
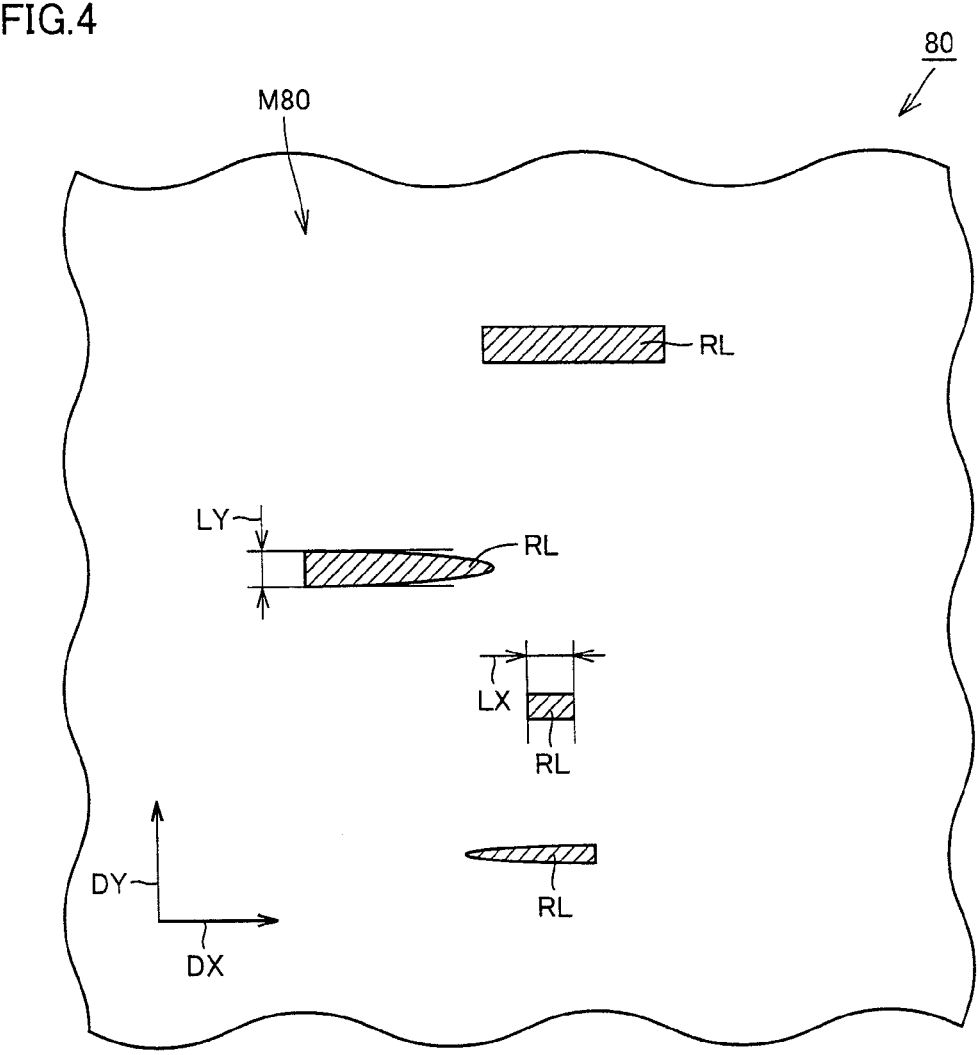
FIG. 4 is a partial plan view schematically showing examples of photoluminescent light emitting regions of the silicon carbide substrate shown in FIG. 1.

As shown in FIG. 4, regions RL emitting photoluminescent light LL is observed. Emitting region RL is a region that emits light of higher intensity than surrounding regions, and it can be observed as a relatively brighter region. Maximum dimensions LX and LY along the directions DX and DY, respectively, are calculated for each emitting region RL. Of the emitting regions RL, the number of those having the dimension LX not larger than a value obtained by dividing penetration length of excitation light LE to the hexagonal crystal silicon carbide by a tangent of off angle OA and having the dimension LY not larger than 15 μm is counted. Then, the obtained number is divided by the area (cm²) of a portion as an object of observation of main surface M80. The resulting value is a characteristic value that serves as an index of photoluminescence characteristics of main surface M80 of single crystal substrate 80. The main surface M80 of single crystal substrate 80 in accordance with the present embodiment has this characteristic value of $1\times10^4/cm^2$ or smaller.

The penetration length represents a length, vertical to the observed main surface, of the light incident on the main surface to a point where its intensity is attenuated to the ratio of 1/e (e is Napier's constant).

Preferably, even if counting of the number of emitting regions RL takes place unconditionally, that is, if the counting is done without the limitation of dimensions LX and LY, main surface M80 still has the value of $1\times10^4$ per 1 cm² or smaller, as the characteristic value.

Next, the method of manufacturing single crystal substrate 80 will be described.

Figure 5:
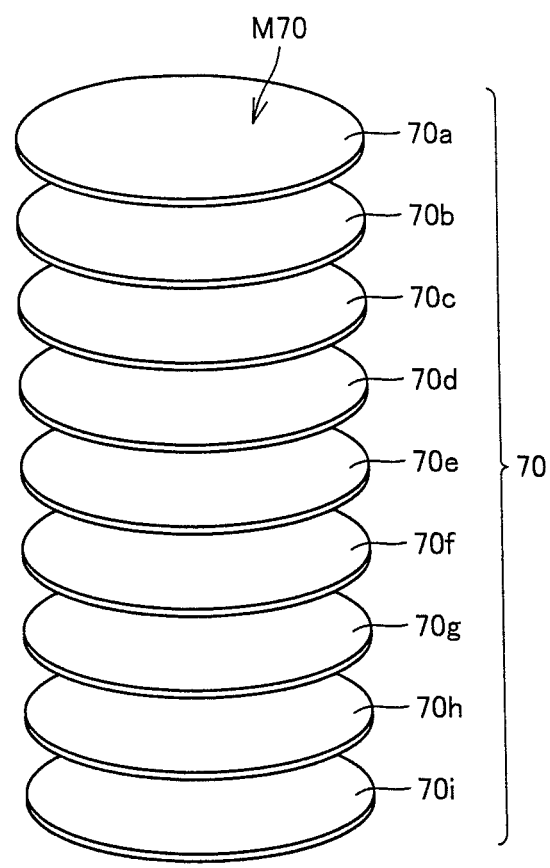
FIG. 5 is a perspective view schematically showing the first step of the method of manufacturing the silicon carbide substrate of FIG. 1.

As shown in FIG. 5, silicon carbide single crystals 70*a* to 70*i* (also generally denoted by 70) each having a main surface M70 are prepared. Silicon carbide single crystal 70 has hexagonal crystal structure and preferably has polytype of 4H. Plane direction of main surface M70 corresponds to plane direction of main surface M80 (FIG. 1). Thickness (dimension in the lengthwise direction in the figure) of silicon carbide single crystal 70 is, for example, 0.5 mm to 10 mm. Planar shape of silicon carbide single crystal 70 is, for example, circular, of which diameter is preferably 25 mm or larger and, more preferably, 100 mm or larger.

Figure 6:
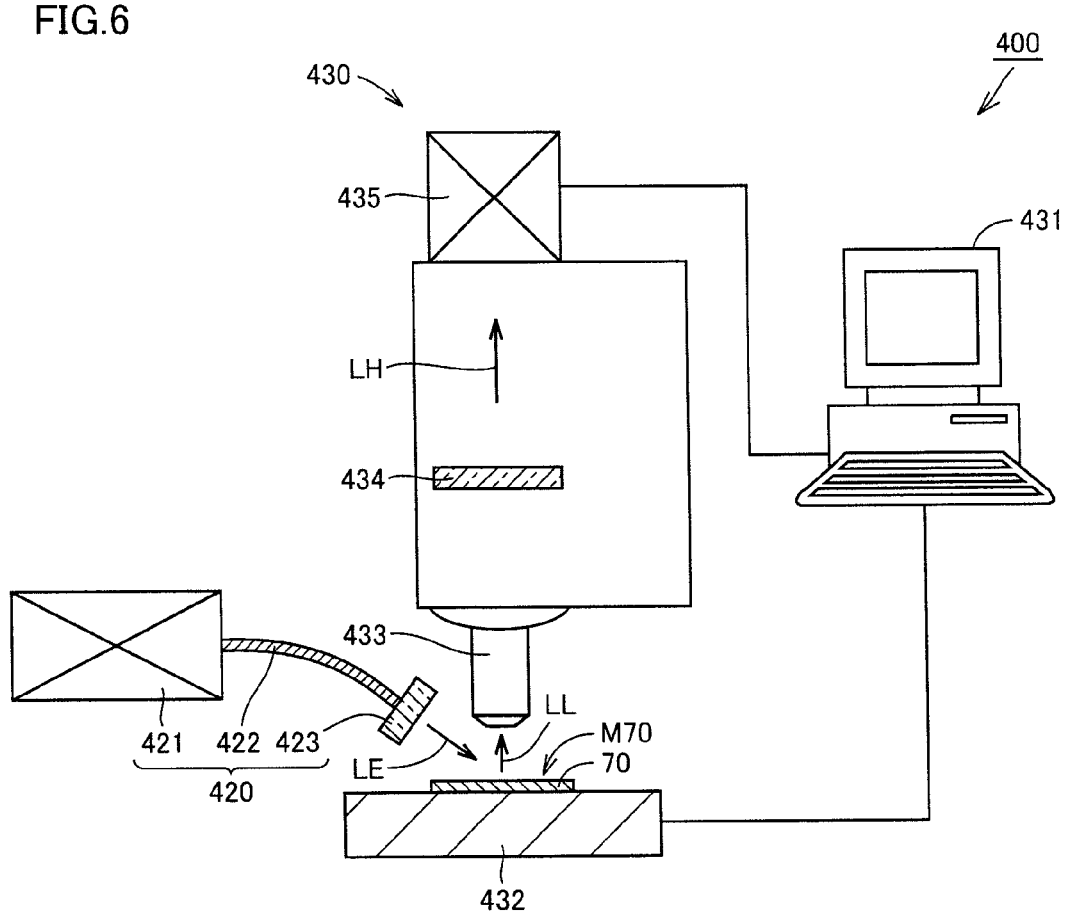
FIG. 6 is a block diagram schematically showing the second step of the method of manufacturing the silicon carbide substrate of FIG. 1.
Figure 7:
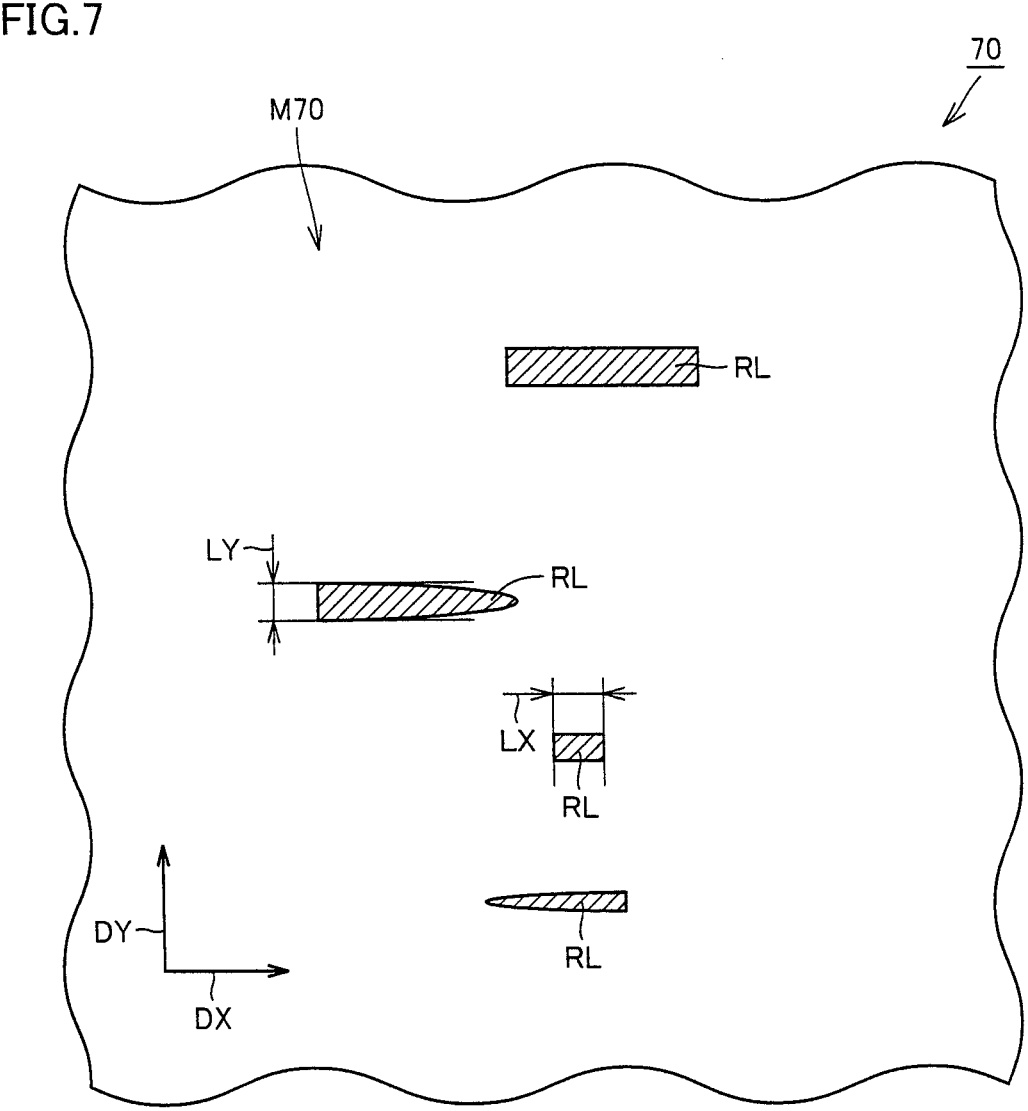
FIG. 7 is a partial plan view schematically showing the third step of the method of manufacturing the silicon carbide substrate of FIG. 1.

As shown in FIGS. 6 and 7, photoluminescence of main surface M70 of each of silicon carbide single crystals 70*a* to 70*i* is measured. Consequently, characteristic value as described with reference to FIGS. 3 and 4 is calculated.

Figure 8:
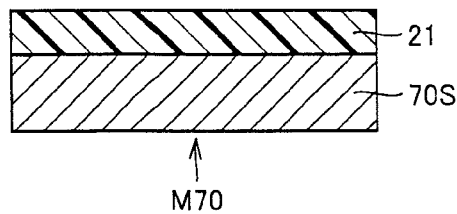
FIG. 8 is a cross-sectional view schematically showing the fourth step of the method of manufacturing the silicon carbide substrate of FIG. 1.

Referring to FIG. 8, of silicon carbide single crystals 70*a* to 70*i*, one having the characteristic value smaller than a prescribed value is selected as a seed crystal 70S. The prescribed value is, for example, the criterion of main surface M80, that is, $1\times10^4/cm^2$.

Next, backside (opposite to main surface M70) of seed crystal 70S is processed to increase surface roughness. This process is done by polishing the backside surface using abrasive particles having sufficiently large particle diameter. Particle size distribution of abrasive particles preferably has a component of 16 μm or larger. Average particle size of abrasive particles is preferably 5 μm to 50 μm, and more preferably 10 μm to 30 μm, and further preferably 12 to 25 μm.

Preferably, the abrasive particles are diamond particles. Further, preferably, the abrasive particles are used dispersed in slurry. Therefore, the polishing mentioned above is preferably conducted using diamond slurry. Generally, diamond slurry containing diamond particles having average particle size of 5 μm to 50 μm and having component of 16 μm in particle distribution is readily available.

Instead of conducting the step of increasing surface roughness of the backside surface of seed crystal 70S, a backside surface having sufficient surface roughness may be formed from the outset, and the backside surface may be used without polishing. Specifically, backside surface of seed crystal 70S formed by slicing with wire saw may be used without polishing. In other words, as the backside surface, as-sliced surface formed by slicing and not subjected to subsequent polishing may be used. Preferably, at the time of slicing with wire saw, the abrasive particles mentioned above are used.

Next, on the backside surface of seed crystal 70S, a coating film 21 including carbon is formed. Preferably, surface roughness of coating film 21 is made smaller than the surface roughness of backside surface of seed crystal 70S on which coating film 21 is formed.

Preferably, the coating film is formed by applying liquid material and, more preferably, the liquid material does not contain any solid matter. Therefore, thin coating film 21 can be formed easily and uniformly.

In the present embodiment, coating film 21 is an organic film. The organic film is preferably formed of an organic resin. As the organic resin, acrylic resin, phenol resin, urea resin or epoxy resin may be used, or resin having composition of photosensitive resin that is cross-linked or decomposed by light may be used. As the photosensitive resin, a positive or negative photoresist used for manufacturing semiconductor devices may be used. Regarding the photoresists, application technique of spin-coating has been established and, therefore, thickness of coating film 21 can be regulated easily. Exemplary manner of spin-coating is as follows.

First, seed crystal 70S is held by suction on a holder. The holder is rotated at a prescribed speed of rotation, so that seed crystal 70S is also rotated. A photoresist is dropped on rotating seed crystal 70S and rotation is continued for a prescribed time period, so that the photoresist is applied thin and uniform. In order to ensure uniformity over the entire surface of seed crystal 70S, the speed of rotation is set, for example, to 1000 to 10000 rpm, time of rotation is set to 10 to 100 seconds and the coating thickness is at least 0.1 µm.

Thereafter, the applied photoresist is dried and solidified. The temperature and time for drying may appropriately be selected in accordance with the material and coating thickness of photoresist. Preferably, the drying temperature is at least 100° C. and at most 400° C., and the drying time is at least 5 minutes and at most 60 minutes. If the drying temperature is 120° C., the time necessary for volatilization is 15 minutes for the thickness of 5 µm, 8 minutes for the thickness of 2 µm and 3 minutes for the thickness of 1 µm.

Though coating film 21 can be formed by once performing the process including the application and drying steps described above, thicker coating film 21 may be formed by repeating the process steps. If the number of repetition is too large, time for this process would be undesirably long and, therefore, typically the repetition of twice or three times is preferred.

Figure 9:
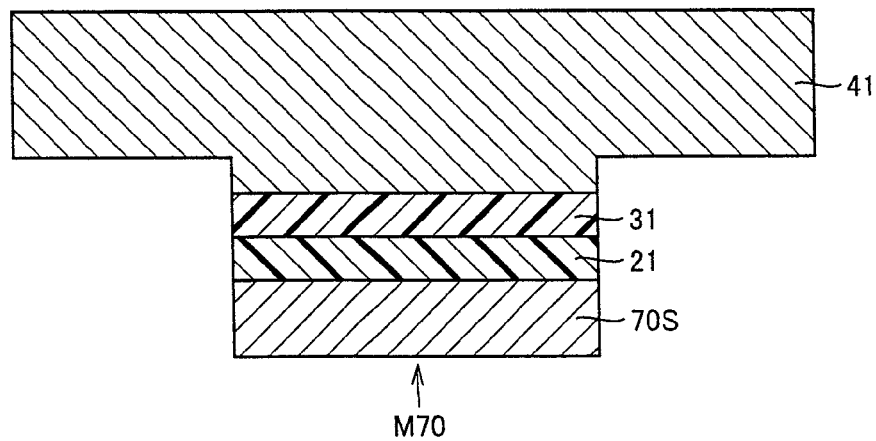
FIG. 9 is a cross-sectional view schematically showing the fifth step of the method of manufacturing the silicon carbide substrate of FIG. 1.

Referring to FIG. 9, a base 41 having a mounting surface, on which seed crystal 70S is mounted, is prepared. The mounting surface preferably includes a surface formed of carbon. By way of example, base 41 is formed of graphite. Preferably, the mounting surface is polished to improve flatness of the mounting surface.

Thereafter, coating film 21 and base 41 are brought into contact with each other with adhesive 31 interposed. Preferably, the contact is attained at a temperature of at least 50° C. and at most 120° C. under pressure of at least 0.01 Pa and at most 1 MPa to press the film and base to each other. Here, adhesive 31 is applied not to run off the edge of the region sandwiched between seed crystal 70S and base 41, so as to prevent undesirable effect of adhesive 31 in the subsequent step of growing single crystal as will be described later.

Preferably, adhesive 31 contains resin that is carbonized to non-graphitizable carbon when heated, heat-resistant fine particles and a solvent and, more preferably, additionally contains carbohydrate.

The resin that turns to non-graphitizable carbon is, for example, novolak resin, phenol resin, or furfuryl alcohol resin.

The heat-resistant fine particles has a function, in a fixing layer formed by high-temperature heating of adhesive 31, of increasing filling rate of the fixing layer by uniformly distributing the non-graphitizable carbon mentioned above. As a material for the heat-resistant fine particles, heat-resistant material such as carbon (C) including graphite, silicon carbide (SiC), boron nitride (BN), or aluminum nitride (AlN) may be used. Other than the above, high-melting point metal or a compound such as a carbide or nitride of such metal may be used as the material. Examples of high-melting point metal may include tungsten (W), tantalum (Ta), molybdenum (Mo), titanium (Ti), zirconium (Zr) and hafnium (Hf). The heat-resistant fine particles have the particle size of, for example, 0.1 to 10 µm.

As carbohydrate, sugar or its derivative may be used. The sugar may be monosaccharide such as glucose or polysaccharide such as cellulose.

As the solvent, any solvent that can solve/disperse the resin and carbohydrate described above may appropriately be selected. The solvent is not limited to one composed of a single type of liquid, and it may be a mixture of a plurality of different liquids. By way of example, a solvent containing alcohol for solving carbohydrate and celosolve acetate for solving resin may be used.

The ratio of resin, carbohydrate, heat-resistant fine particles and solvent in adhesive 31 is appropriately selected to attain proper adhesion of seed crystal 70S and fixing strength. Further, adhesive 31 may contain a component other than those mentioned above and, by way of example, it may contain additives such as a surface-active agent and a stabilizer. The amount of application of adhesive 31 is, preferably, at least 10 mg/cm$^2$ to at most 100 mg/cm$^2$. The thickness of adhesive 31 is, preferably, at most 100 µm and more preferably, at most 50 µm.

Next, preferably, pre-baking of adhesive 31 takes place. Preferable temperature of pre-baking is at least 150° C.

Figure 10:
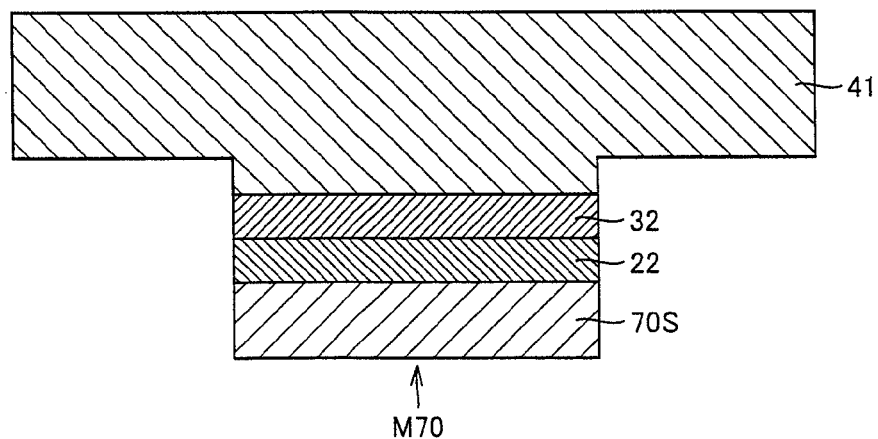
FIG. 10 a cross-sectional view schematically showing the sixth step of the method of manufacturing the silicon carbide substrate of FIG. 1.

Referring to FIG. 10, coating film 21 and adhesive 31 (FIG. 9) are heated. By the heating, coating film 21 is carbonized and turns to carbon film 22. In other words, a carbon film 22 forms on seed crystal 70S. By the heating, adhesive 31 is cured between carbon film 22 and base 41 and forms a fixing layer 32. Thus, seed crystal 70S is fixed on base 41.

Preferably, the heating mentioned above is done at a temperature of at least 800° C. and at most 1800° C., for at least one hour and at most 10 hours, with a pressure of at least 0.13 kPa and at most the atmospheric pressure, in an inert gas atmosphere. By way of example, helium, argon or nitrogen gas is used as the inert gas.

In the step described above, when adhesive 31 is cured, coating film 21 is carbonized. Coating film 21 may be carbonized before forming adhesive 31.

Figure 11:
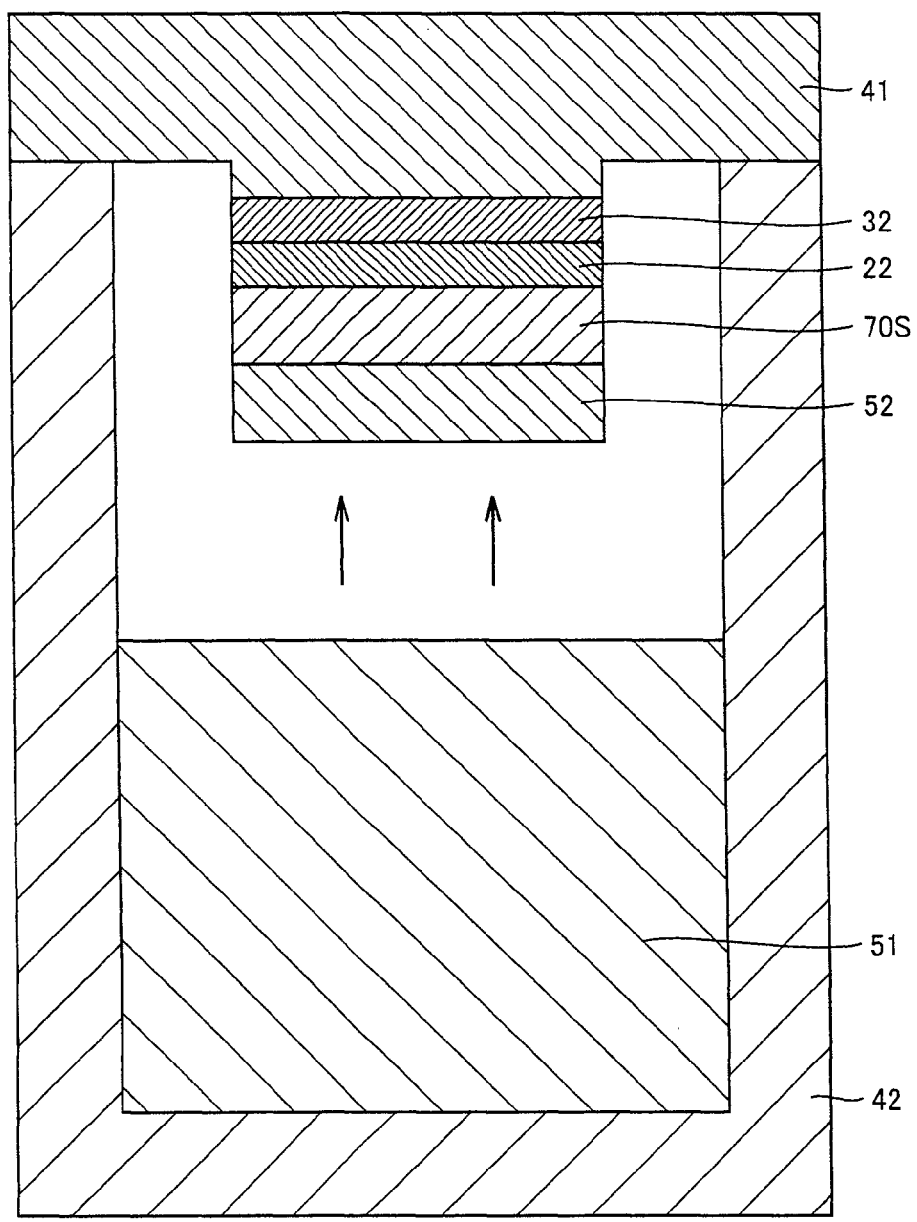
FIG. 11 a cross-sectional view schematically showing the seventh step of the method of manufacturing the silicon carbide substrate of FIG. 1.

Referring to FIG. 11, a raw material 51 is placed in a crucible 42. Raw material 51 is, for example, silicon carbide powder. Crucible 42 is formed, for example, of graphite. Then, base 41 is mounted such that seed crystal 70S is positioned facing the inside of crucible 42. As shown in FIG. 11, base 41 may function as a lid of crucible 42.

Next, raw material 51 is sublimated and re-crystallized on seed crystal 70S as represented by arrows in the figure, and the sublimate deposits on seed crystal 70S. Thus, an ingot 52 is formed on seed crystal 70S. The temperature for sublimating and re-crystallizing silicon carbide is set, for example, to at least 2100° C. and at most 2500° C. Further, temperature gradient is provided in crucible 42 such that the temperature of seed crystal 70S is lower than the temperature of raw material 51. Pressure in crucible 42 is preferably set to at least 1.3 kPa and at most the atmospheric pressure and, more preferably, at most 13 kPa to increase growth rate.

Figure 12:
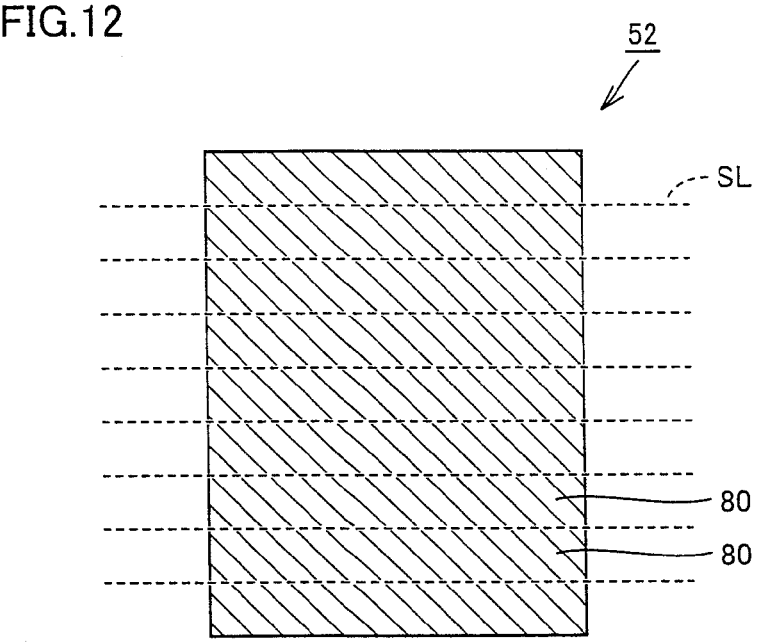
FIG. 12 a cross-sectional view schematically showing the eighth step of the method of manufacturing the silicon carbide substrate of FIG. 1.

As shown in FIG. 12, ingot 52 is sliced. Thus, single crystal substrate 80 (FIG. 1) is obtained.

According to the present embodiment, photoluminescence characteristics of main surface 80M of single crystal substrate 80 have the characteristic value described above. By manufacturing a semiconductor device that should desirably have small reverse leakage current such as a Schottky diode or an MOSFET (Metal Oxide Semiconductor Field Effect Transistor) as will be described later using single crystal substrate 80, the reverse leakage current can be made smaller.

Growth conditions such as temperature, pressure and temperature gradient when ingot 52 is grown are optimized in accordance with facilities used in the actual mass-production process. If the optimization is inappropriate, the photoluminescence characteristics may fail to have the desired characteristic value. In that case, the growth conditions can be adjusted to attain the desired characteristic value.

The maximum dimension of single crystal substrate 80 is preferably at least 75 mm and more preferably, at least 100 mm. By way of example, single crystal substrate 80 is a circular wafer having the diameter of at least 100 mm. Using such a large wafer, semiconductor devices having small reverse leakage current can be manufactured with high efficiency.

Embodiment 2

Figure 13:
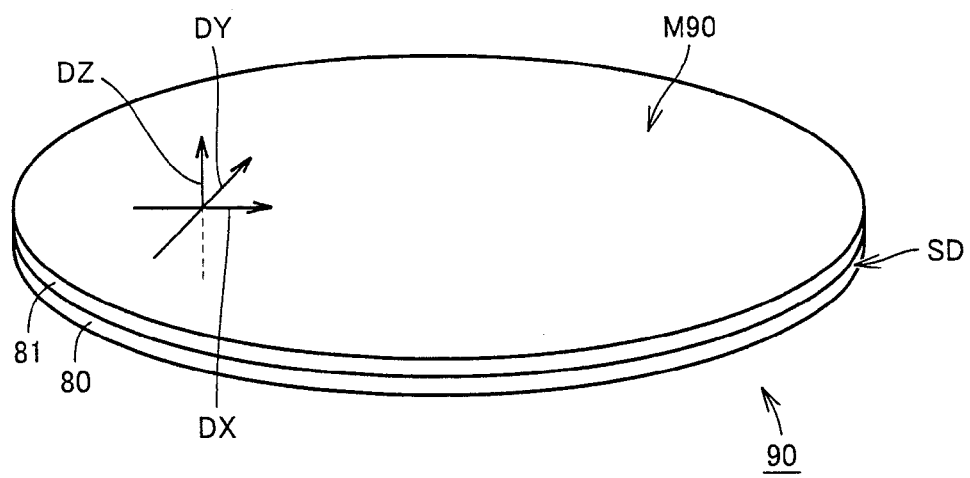
FIG. 13 is a perspective view schematically showing a structure of a silicon carbide substrate in accordance with Embodiment 2 of the present invention.

As shown in FIG. 13, the silicon carbide substrate in accordance with the present embodiment is an epitaxial substrate 90 (silicon carbide substrate) having a silicon carbide layer 81 with a main surface M90 and a single crystal substrate 80 (base substrate) supporting silicon carbide layer 81. Silicon carbide layer 81 is epitaxially formed on single crystal substrate 80.

Main surface M90 of epitaxial substrate 90 has specific photoluminescence characteristics as described later. A method of measuring photoluminescence characteristics will be described in the following.

Figure 14:
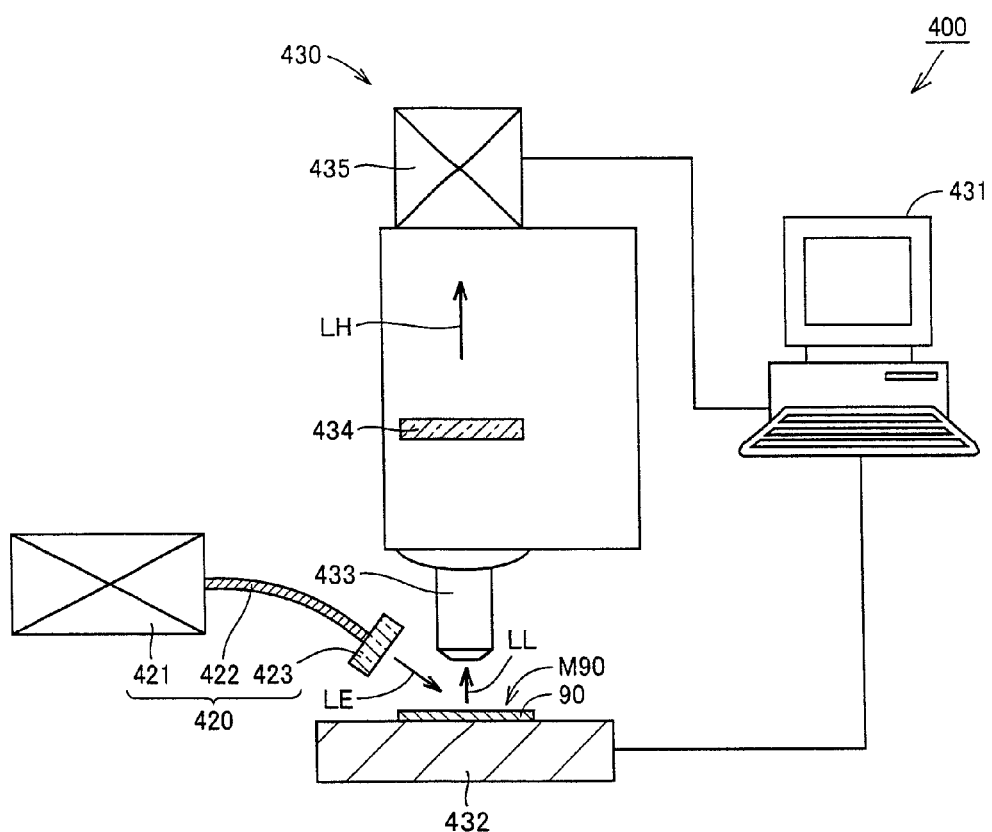
FIG. 14 is a block diagram schematically showing a configuration of a measuring apparatus used for photoluminescence measurement of the silicon carbide substrate shown in FIG. 13.

As shown in FIG. 14, epitaxial substrate 90 is mounted on a photoluminescence measuring apparatus 400. Main surface M90 of epitaxial substrate 90 is irradiated with excitation light LE. Consequently, emission of photoluminescent light LL occurs on main surface M90. Transmitted light LH, which is photoluminescent light LL passed through filter 434, is observed as an image by camera 435. Specifically, on main surface M90, emitting regions emitting photoluminescent light LL having a wavelength longer than 650 nm are observed. Which range of the wavelength exceeding 650 nm is observed is determined by characteristics of filter 434.

Figure 15:
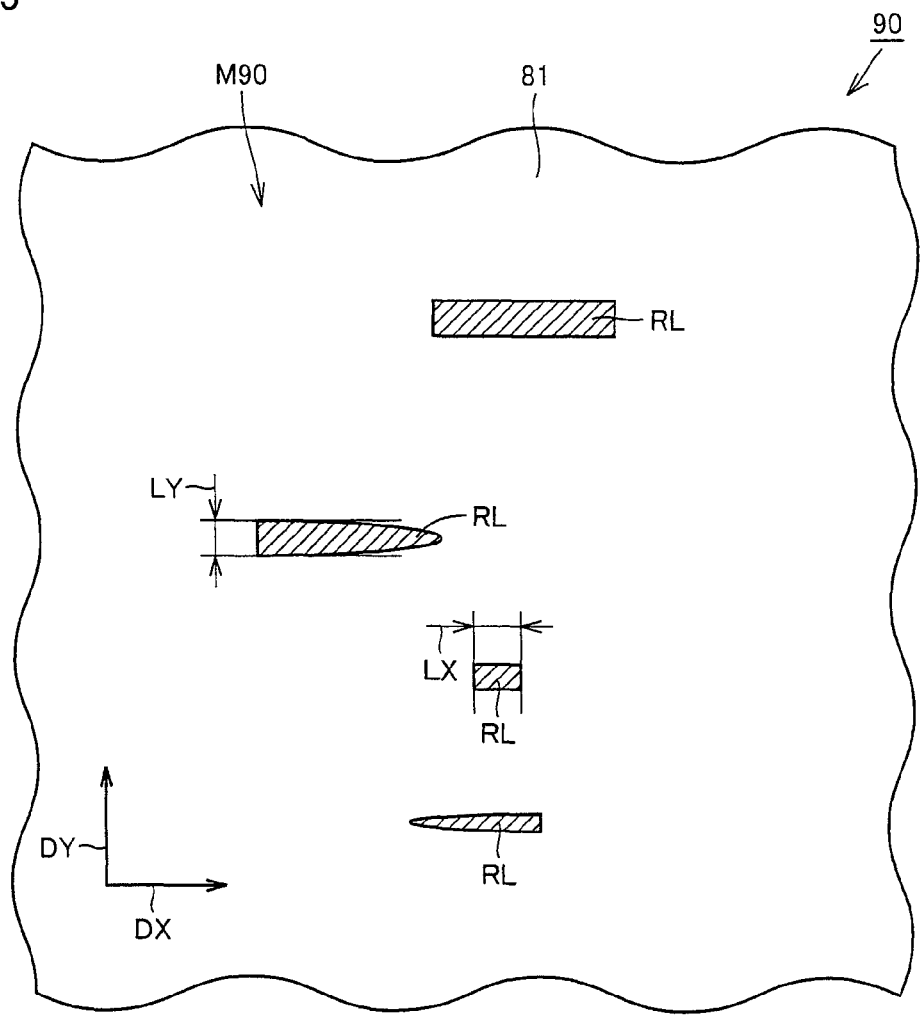
FIG. 15 is a partial plan view schematically showing examples of photoluminescent light emitting regions of the silicon carbide substrate shown in FIG. 13.

As shown in FIG. 15, maximum dimensions LX and LY along the directions DX and DY, respectively, are calculated for each emitting region RL. Of the emitting regions RL, the number of those having the dimension LX not larger than a value obtained by dividing penetration length of excitation light LE to the hexagonal crystal silicon carbide by a tangent of off angle OA and having the dimension LY not larger than 15 μm is counted. Then, the obtained number is divided by the area (cm$^2$) of a portion as an object of observation of main surface M90. The resulting value is a characteristic value that serves as an index of photoluminescence characteristics of main surface M90 of epitaxial substrate 90. The main surface M90 of epitaxial substrate 90 in accordance with the present embodiment has this characteristic value of $1\times10^4/\text{cm}^2$ or smaller.

Preferably, even if counting of the number of emitting regions RL takes place unconditionally, that is, if the counting is done without the limitation of dimensions LX and LY, main surface M90 still has the value of $1\times10^4$ per 1 cm$^2$ or smaller, as the characteristic value.

Except for the points described above, the configuration is substantially the same as that of Embodiment 1 above and, therefore, the same or corresponding components are denoted by the same reference characters and description thereof will not be repeated.

Figure 16:
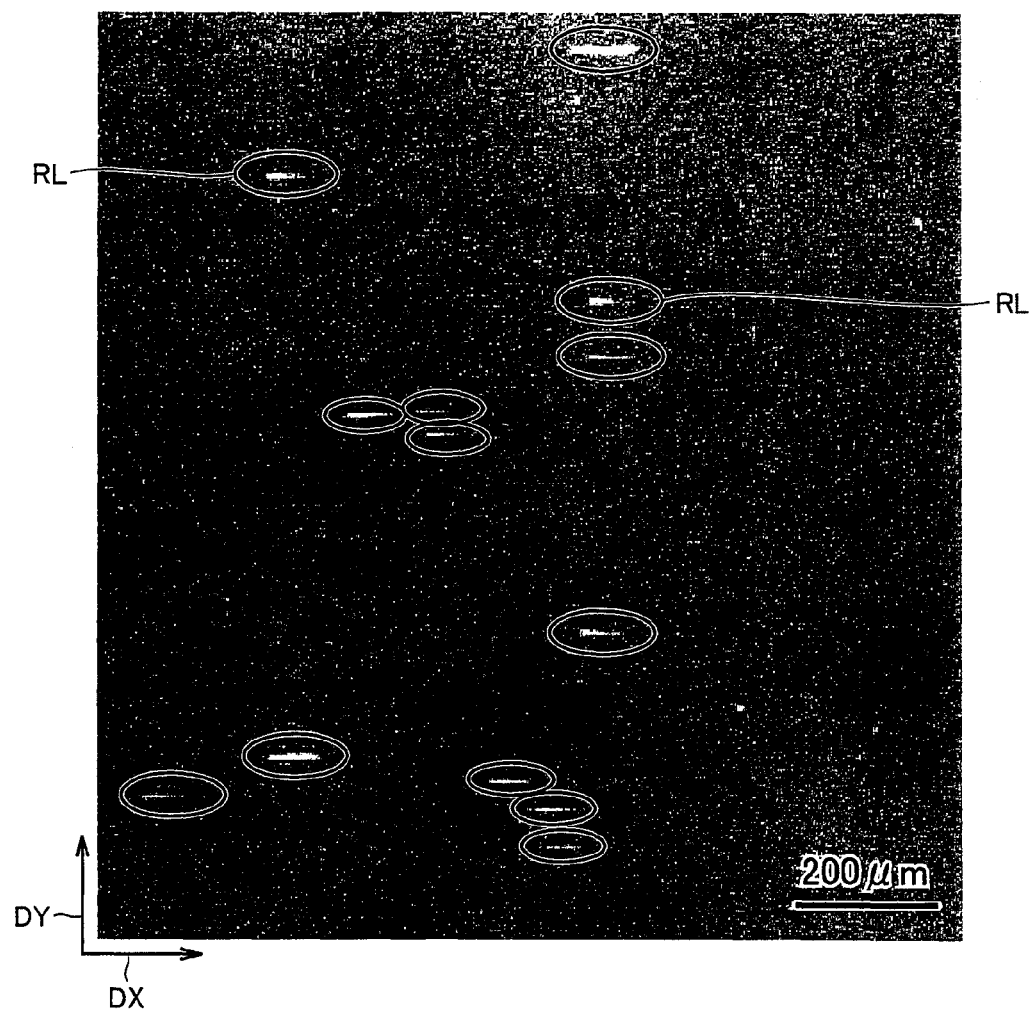
FIG. 16 is a microscopic photograph schematically showing examples of photoluminescent light emitting regions of the silicon carbide substrate shown in FIG. 13.

Referring to FIG. 16, an example of the result of photoluminescence measurement will be described in the following.

A single crystal substrate 80 having polytype 4H crystal structure was prepared. Main surface M80 of single crystal substrate 80 has an off angle OA (FIG. 2) of 8 degrees from (0001) plane. Silicon carbide layer 81 of 10 μm in thickness was formed on main surface M80.

Photoluminescence of main surface M90 of silicon carbide layer 81 was measured (FIG. 14). Light emitted from a mercury lamp and passed through band-pass type filter 423 particularly passing light having the wavelength of about 313 nm was used as excitation light LE for measurement. Images of photoluminescent light LL caused by excitation light LE were picked up through filter 434 that particularly passes light having a wavelength of 750 nm or longer (a filter particularly prevents passage of light having cutoff wavelength shorter than 750 nm), whereby emitting regions RL were observed (FIG. 16). Typical dimension of emitting regions RL was about 50 μm in the off direction DX and at most 15 μm and about 10 μm in average in direction DY perpendicular to off direction DX.

Easiness of observing emitting regions RL depends on the characteristics of filter 434, and without filter 434, accurate observation of emitting regions RL was impossible.

When the incident angle of excitation light LE to main surface M90 was changed, the dimension of emitting regions RL hardly changed in direction DY while the dimension becomes smaller as the incident angle becomes larger in direction DX. Specifically, the dimension in direction DX was in proportion to inverse tangent of the incident angle.

Maximum dimensions LX and LY along the directions DX and DY, respectively, were calculated for each emitting region RL. Of the emitting regions RL, the number of those having the dimension LX not larger than a value obtained by dividing penetration length of excitation light LE to the hexagonal crystal silicon carbide by a tangent of off angle OA and having the dimension LY not larger than 15 μm was counted. Then, the obtained number was divided by the area (cm$^2$) of a portion as an object of observation of main surface M80. In Schottky diodes fabricated by using samples (epitaxial substrate 90 as an example of the invention) having the resulting value (characteristic value) of $1\times10^4/\text{cm}^2$ or smaller, no abnormality in reverse leakage current was observed. In contrast, in Schottky diodes fabricated by using samples (epitaxial substrate as a comparative example) having the characteristic value exceeding $1\times10^4/\text{cm}^2$, reverse leakage current sometimes became abnormally high. Possible reason is as follows. If defects, which are detected by the photoluminescence measurement, exist on an outer periphery of a diode, reverse leakage current sometimes tends to be large, and if the characteristic value exceeds $1\times10^4/\text{cm}^2$, the number of defects tends to increase at the outer peripheral portion.

Figure 17:
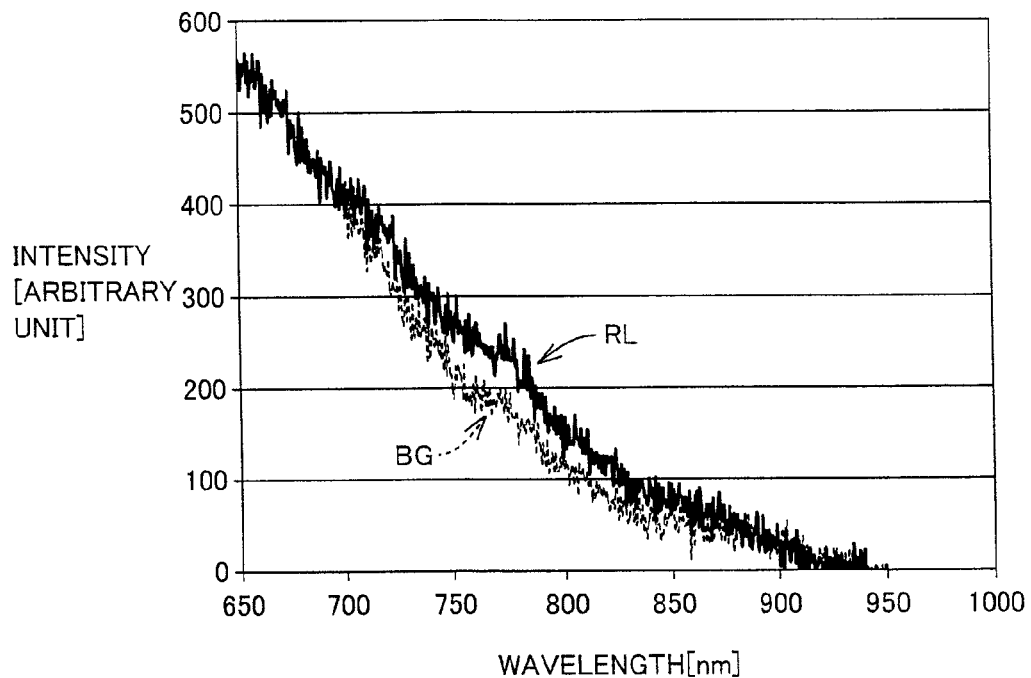
FIG. 17 is a graph showing an exemplary relation between photoluminescent light wavelength and intensity in the emitting region and other region, respectively, in the silicon carbide substrate shown in FIG. 13.

Referring to FIG. 17, spectrum of photoluminescent light LL from emitting region RL of main surface M90 and the spectrum of photoluminescent light LL from other regions on main surface M90 were compared, in the range of wavelength from 650 nm to 950 nm (FIG. 17). The spectrum of emitting region RL had higher intensity in a specific wavelength range than the spectrum of other regions BG. The difference in intensity is considered to be the reason why emitting region RL is brighter than the surrounding regions. The wavelength range was between 650 nm and 950 nm. Further, intensity was higher in a lower wavelength range. Therefore, it is considered preferable for highly accurate observation of emitting regions RL, to remove light having the wavelength outside the above-described wavelength range and, particularly, to remove light having a wavelength shorter than the wavelength range. Further, since the difference in intensity between the spectra was significantly large at the range exceeding 750 nm, use of a filter that passes light exceeding 750 nm is preferable.

As described above, according to the present embodiment, photoluminescence characteristic of main surface M90 of epitaxial substrate 90 has the above-described characteristic value. By manufacturing a semiconductor device that should desirably have small reverse leakage current such as a Schottky diode or an MOSFET (Metal Oxide Semiconductor Field Effect Transistor) as will be described later using epitaxial substrate 90, the reverse leakage current can be made smaller.

In the present embodiment, what is necessary is that main surface M90 of silicon carbide layer 81 has the desired photoluminescence characteristic, and photoluminescence characteristic of main surface M80 of single crystal substrate 80 may not necessarily satisfy the criterion described in Embodiment 1. If main surface M80 of single crystal substrate 80 satisfies the criterion described in Embodiment 1, however, desired photoluminescence characteristic can be imparted more reliably on the main surface M90 of silicon carbide layer 81.

Embodiment 3

Figure 18:
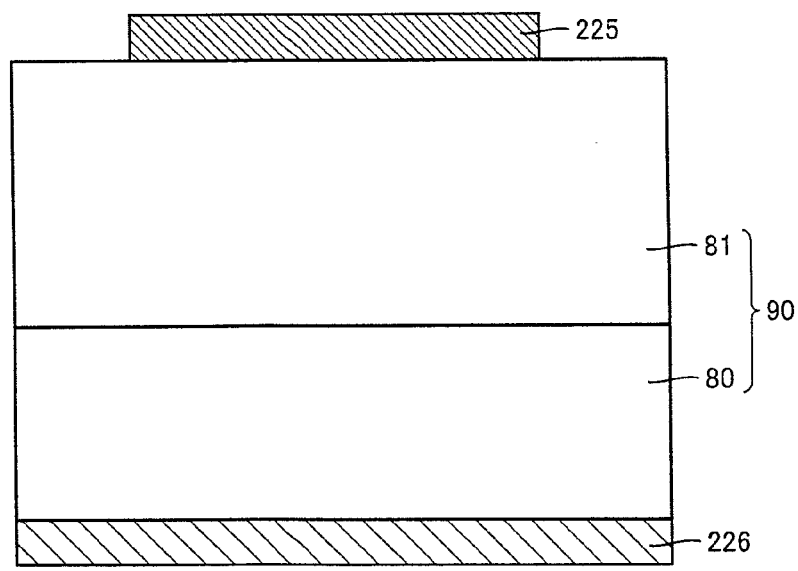
FIG. 18 is a cross-sectional view schematically showing a structure of a semiconductor device in accordance with Embodiment 3 of the present invention.

As shown in FIG. 18, a semiconductor device in accordance with the present embodiment is a Schottky diode 500 (semiconductor device) having epitaxial substrate 90. Schottky diode 500 has epitaxial substrate 90, an anode electrode 225 and a cathode electrode 226. Anode electrode 225 is provided on a main surface on the side of silicon carbide layer 81 of epitaxial substrate 90. The cathode electrode is provided on a surface on the side of single crystal substrate 80 of epitaxial substrate 90.

Single crystal substrate 80 has n$^+$ conductivity type, and silicon carbide layer 81 has n$^-$ conductivity type. Thickness of single crystal substrate 80 is, for example, at least 300 μm and at most 400 μm. By way of example, single crystal substrate 80 contains nitrogen atoms as an impurity, of which concentration is about $1 \times 10^{19}$ cm$^{-3}$. The thickness of silicon carbide layer 81 is, for example, 10 μm. By way of example, silicon carbide layer 81 contains nitrogen atoms as an impurity, of which concentration is about $5 \times 10^{15}$ cm$^{-3}$.

Anode electrode 225 is formed of metal material that can establish Schottky contact with silicon carbide layer 81 where no voltage is applied to the electrode. Cathode electrode 226 is formed of metal material that can establish ohmic contact with single crystal substrate 80.

Operation of Schottky diode 500 will be described. At a contact portion between anode electrode 225 and silicon carbide layer 81, a Schottky barrier is formed. Therefore, if no voltage is applied or a negative voltage is applied to anode electrode 225, even if a potential difference is created between anode electrode 225 and cathode electrode 226, it is difficult to cause a current flow between these electrodes, since depletion layer extends in silicon carbide layer 81 because of the Schottky barrier.

On the other hand, if a positive voltage is applied to anode electrode 225, the Schottky barrier is eliminated in accordance with the magnitude of applied voltage and the depletion layer in silicon carbide layer 81 also disappears. If a potential difference is created between anode electrode 225 and cathode electrode 226 at this time, current flows between these electrodes. From the principle described above, Schottky diode 500 has rectifying property.

Next, a method of manufacturing Schottky diode 500 will be described.

Figure 19:
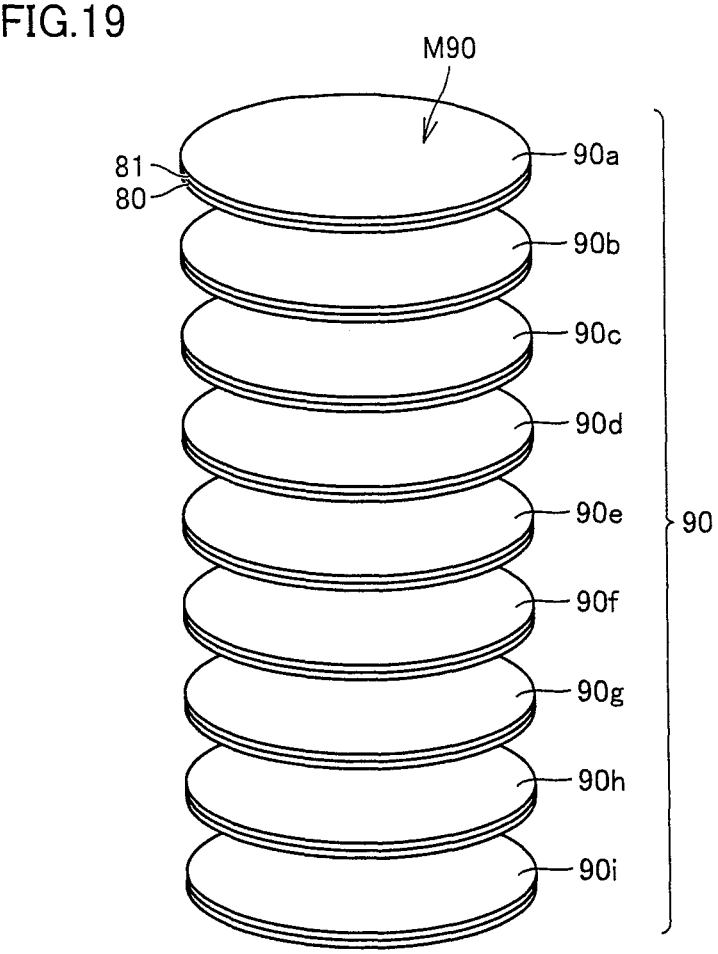
FIG. 19 is a perspective view schematically showing the first step of the method of manufacturing the semiconductor device shown in FIG. 18.

As shown in FIG. 19, a plurality of single crystal substrates 80 are prepared. Preferably, each of the single crystal substrates 80 has the photoluminescence characteristics described with reference to Embodiment 1. Next, on the main surface of each single crystal substrate 80, silicon carbide layer 81 is formed, whereby epitaxial substrates 90a to 90i having similar structure as epitaxial substrate 90 (FIG. 13) are formed.

Thereafter, photoluminescence of main surface M90 of each of epitaxial substrates 90a to 90i is measured. The process of measuring photoluminescence is the same as that of Embodiment 2 (FIG. 14). Consequently, whether or not there is any defective region in which the number of emitting regions per unit area is larger than a prescribed number on main surface M90 is determined. Preferably, the criterion for the number of emitting regions is the same as that described with reference to Embodiment 2.

Figure 20:
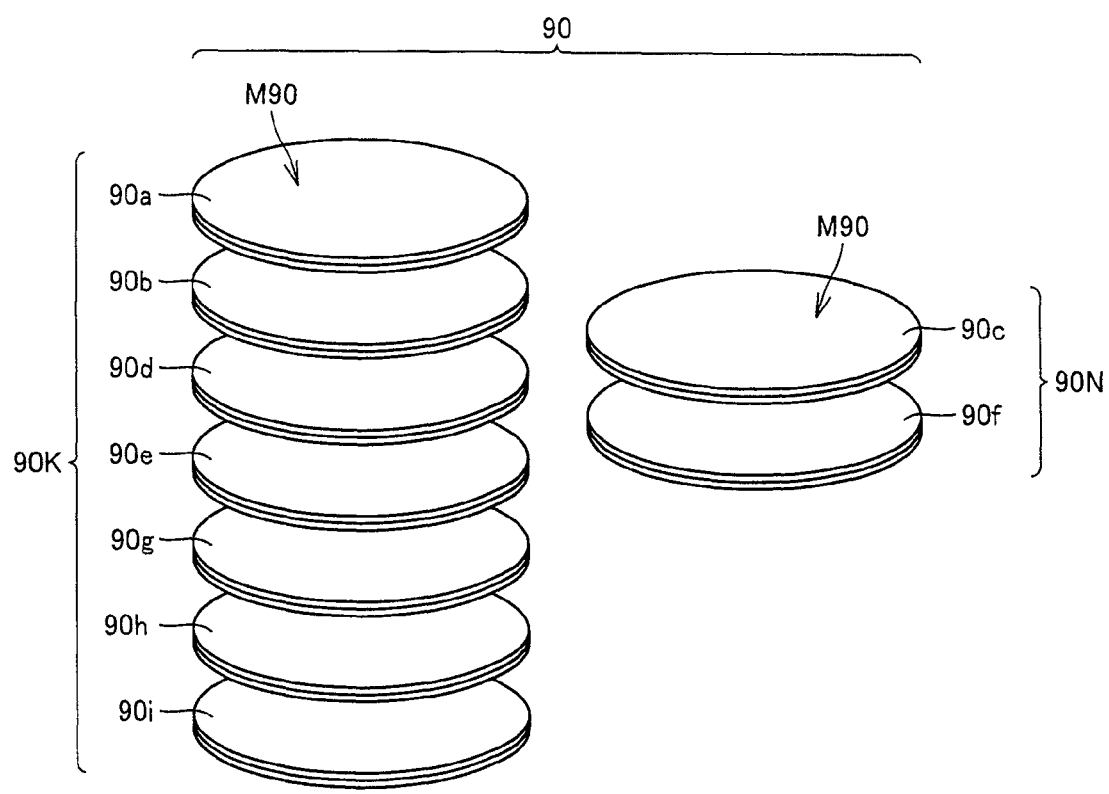
FIG. 20 is a perspective view schematically showing the second step of the method of manufacturing the semiconductor device shown in FIG. 18.

As shown in FIG. 20, of epitaxial substrates 90a to 90i, those having a defective region (in the example of FIG. 20, epitaxial substrates 90c and 90f) are found to be defective substrates 90N, and those not having any defective region are found to be non-defective substrates 90K. Defective substrates 90N are removed from the manufacturing process of Schottky diode 500. Consequently, from the set of main surfaces M90 of epitaxial substrates 90a to 90i, that is, from the fabrication regions for fabricating Schottky diodes 500, defective regions are removed.

Figure 21:
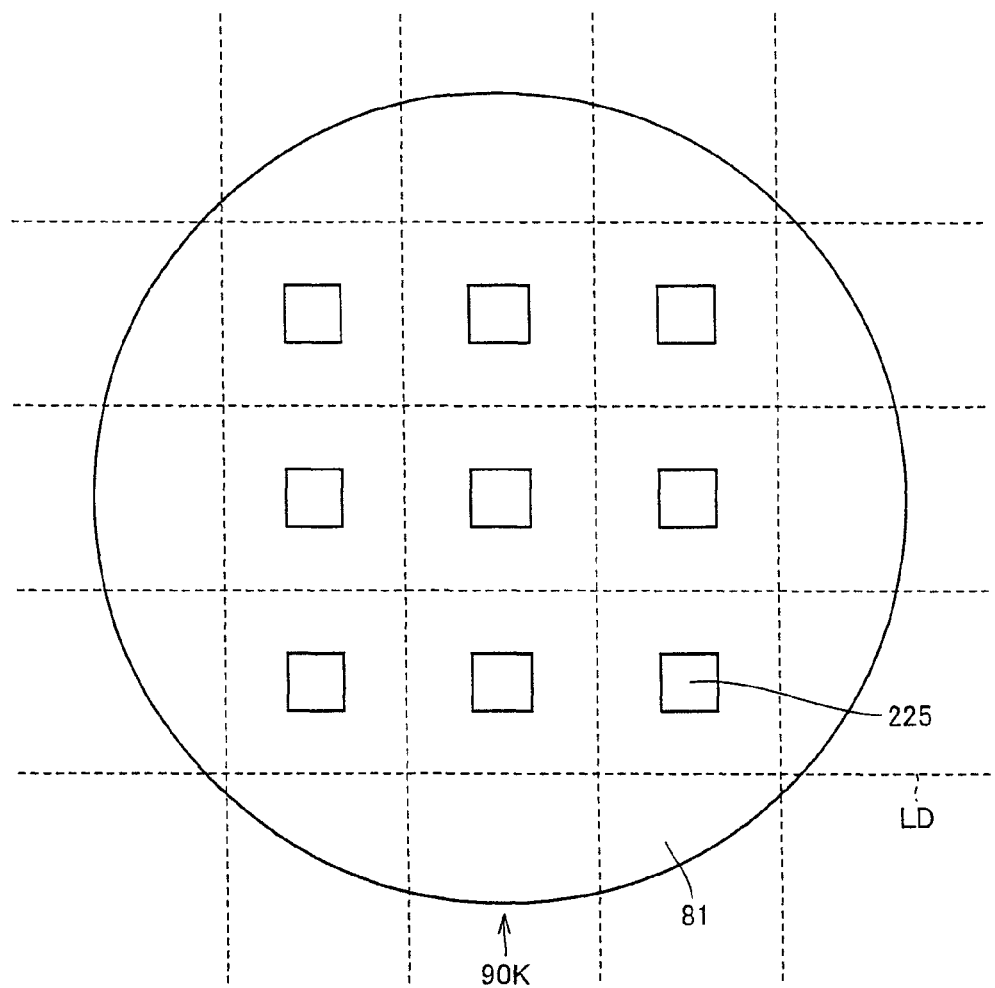
FIG. 21 is a plan view schematically showing the third step of the method of manufacturing the semiconductor device shown in FIG. 18.

As shown in FIG. 21, on silicon carbide layer 81 of each of non-defective substrate 90K, a plurality of anode electrodes 225 are formed. On single crystal substrate 80 (not shown in FIG. 21) of each of non-defective substrate 90, a cathode electrode 226 is formed. Thereafter, non-defective substrate 90K is diced along dotted lines LD in the figure, and a plurality of Schottky diodes 500 are obtained.

Except for the points described above, the configuration is substantially the same as that of Embodiment 1 or 2 above and, therefore, the same or corresponding components are denoted by the same reference characters and description thereof will not be repeated.

Next, a modification of the above-described method of manufacturing Schottky diode 500 will be described.

First, epitaxial substrate 90 is formed in the similar manner as the method described above (FIG. 19).

Figure 22:
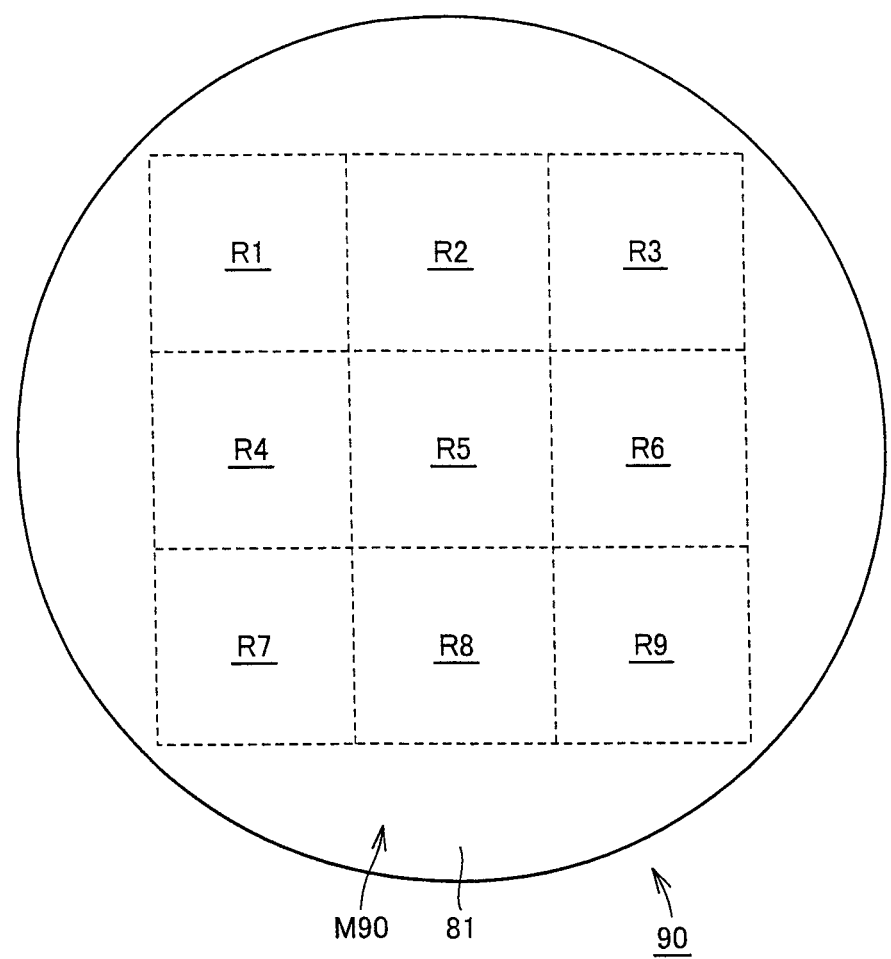
FIG. 22 is a plan view schematically showing the first step of a modification of the method of manufacturing the semiconductor device shown in FIG. 18.

As shown in FIG. 22, presence/absence of the above-described defective region is checked by photoluminescence measurement of each of regions R1 to R9 on main surface M90 of epitaxial substrate 90.

Figure 23:
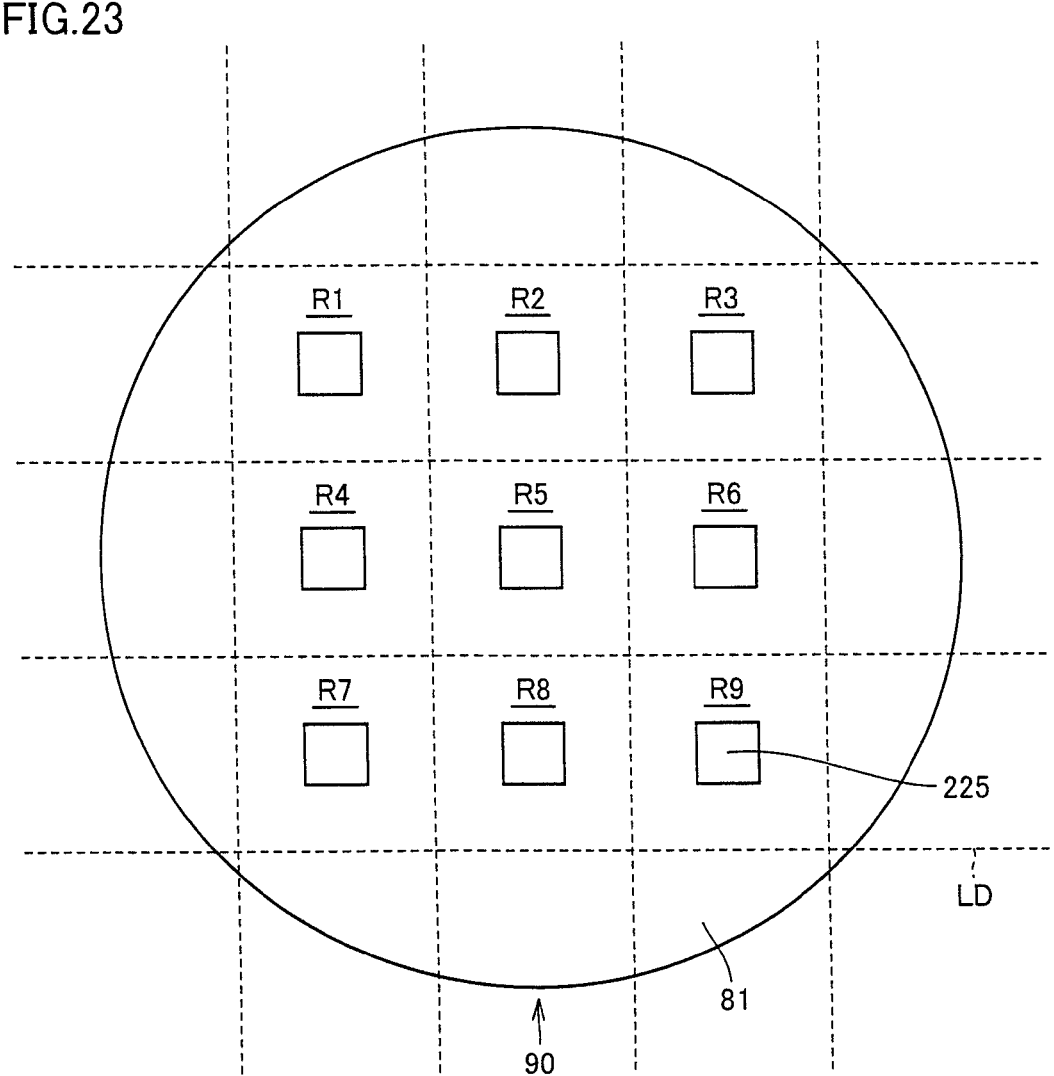
FIG. 23 is a plan view schematically showing the second step of a modification of the method of manufacturing the semiconductor device shown in FIG. 18.

As shown in FIG. 23, anode electrode 225 is formed on each of regions R1 to R9. Further, cathode electrode 226 is formed on single crystal substrate 80 (not shown in FIG. 23) of epitaxial substrate 90. Epitaxial substrate 90 is diced along dotted lines LD in the figure. Though anode electrode 225 is formed unconditionally on each of regions R1 to R9 in the present embodiment, anode electrode 225 may not be formed on any of regions R1 to R9 that has a defective region.

Figure 24:
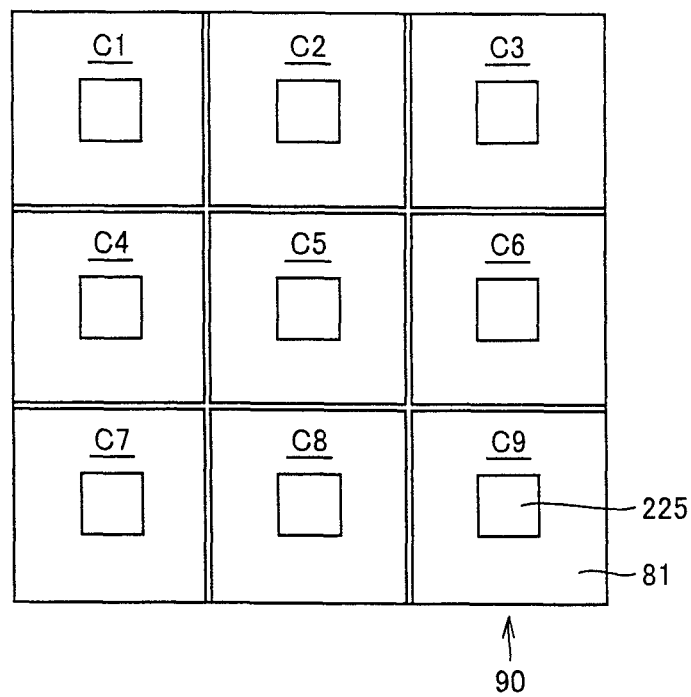
FIG. 24 is a plan view schematically showing the third step of a modification of the method of manufacturing the semiconductor device shown in FIG. 18.

As shown in FIG. 24, by the dicing described above, chips C1 to Cp are formed from regions R1 to R9 (FIGS. 22 and 23), respectively. Next, based on the results of already effected photoluminescence measurements (FIG. 22) of regions R1 to R9, any chip including a defective region is removed from resulting chips C1 to C9. Specifically, of the regions R1 to R9 of epitaxial substrate 90 possibly having a defective region or defective regions, those having any defective region are removed from the manufacturing process of Schottky diode 500. Consequently, defective regions are removed from the fabrication region for fabricating Schottky diodes 500. Further, regions other than the defective region, that is, regions not having any defective region among regions R1 to R9 are determined to be the fabrication regions. Thus, Schottky diodes 500 are formed from regions not having any defective region, of epitaxial substrate 90.

According to the embodiment and its modification, reverse leakage current in Schottky diode 500 can be reduced.

Embodiment 4

Figure 25:
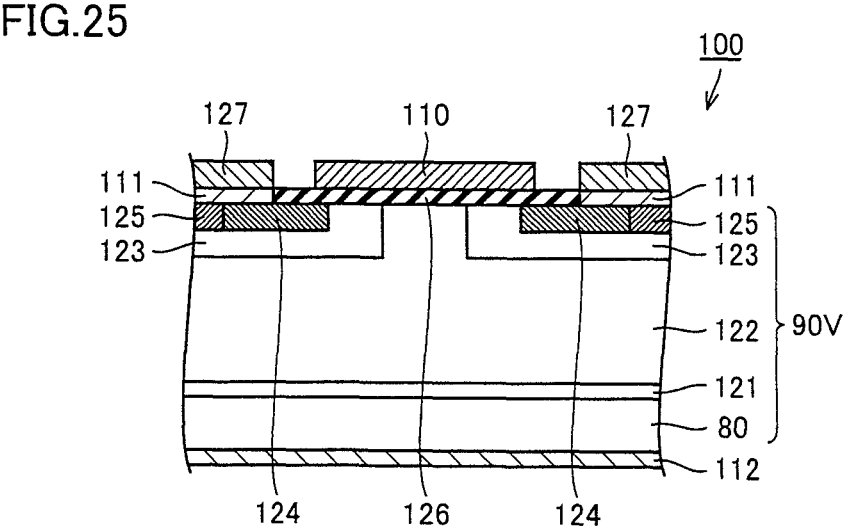
FIG. 25 is a cross-sectional view schematically showing a structure of a semiconductor device in accordance with Embodiment 4 of the present invention.

As shown in FIG. 25, the semiconductor device in accordance with the present embodiment is an MOSFET 100 and, more specifically, it is a vertical DiMOSFET (Double Implanted MOSFET). MOSFET 100 includes an epitaxial substrate 90V, an oxide film 126, a source electrode 111, an upper source electrode 127, a gate electrode 110 and a drain electrode 112. Epitaxial substrate 90V has single crystal substrate 80, a buffer layer 121, a breakdown voltage holding layer 122, a p region 123, an n$^+$ region 124 and a p$^+$ region 125.

Single crystal substrate 80 and buffer layer 121 have n type conductivity. Impurity concentration of n type conductivity in buffer layer 121 is, for example, $5 \times 10^{17}$ cm$^{-3}$. Thickness of buffer layer 121 is, for example, 0.5 μm.

Breakdown voltage holding layer 122 is formed of silicon carbide having n type conductivity, on buffer layer 121. By way of example, breakdown voltage holding layer 122 has a thickness of 10 μm and concentration of n conductivity type impurity is $5 \times 10^{15}$ cm$^{-3}$.

On a surface of breakdown voltage holding layer 122, a plurality of p regions 123 having p type conductivity are formed spaced apart from each other. In p region 123, an n$^+$ region 124 is formed at a surface layer of p region 123. Further, at a position adjacent to n$^+$ region 124, p$^+$ region 125 is formed. On breakdown voltage holding layer 122 exposed between the plurality of p regions 123, oxide film 126 is formed. Specifically, extending from above n$^+$ region 124 on one p region 123, over p region 123, breakdown voltage holding layer 122 exposed between two p-regions 123, the other p region 123 and above n$^+$ region 124 in the said the other p region 123, oxide film 126 is formed. On oxide film 126, gate electrode 110 is formed. Further, on n$^+$ region 124 and p$^+$ region 125, source electrode 111 is formed. On source electrode 111, an upper source electrode 127 is formed.

In a region within 10 nm from the interface between oxide film 126 and each of the semiconductor layers, that is, n$^+$ region 124, p$^+$ region 125, p region 123, and breakdown voltage holding layer 122, the highest concentration of nitrogen atoms is at least $1 \times 10^{21}$ cm$^{-3}$. Therefore, mobility particularly at the channel region below oxide film 126 (the portion of p region 123 in contact with oxide film 126 between n$^+$ region 124 and breakdown voltage holding layer 122) can be improved.

Next, the method of manufacturing MOSFET 100 will be described.

Figure 26:
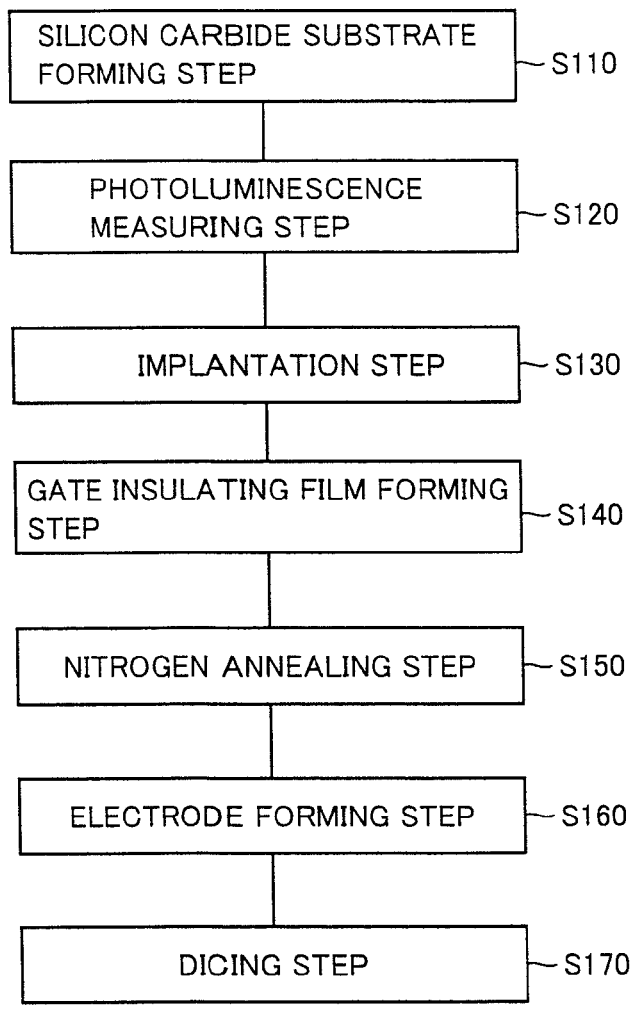
FIG. 26 is a schematic flowchart representing the method of manufacturing the semiconductor device shown in FIG. 24.
Figure 27:
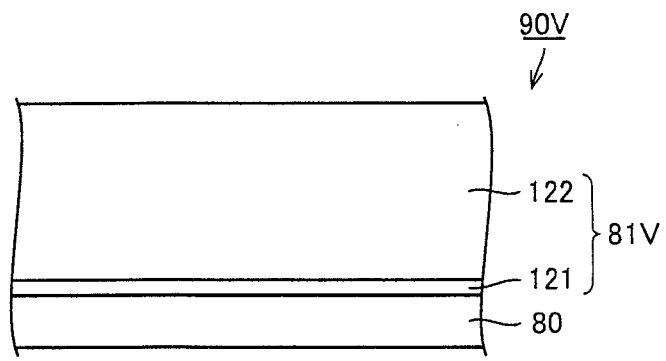
FIG. 27 is a partial cross-sectional view schematically showing the first step of the method of manufacturing the semiconductor device shown in FIG. 25.

As shown in FIG. 27, by epitaxial growth on the main surface of single crystal substrate 80, silicon carbide layer 81V is formed. Specifically, on the main surface of single crystal substrate 80, buffer layer 121 is formed, and on buffer layer 121, breakdown voltage holding layer 122 is formed. Thus, epitaxial substrate 90V is formed (FIG. 26: step 110). Buffer layer 121 is formed of silicon carbide having n type conductivity, and its thickness is about 0.5 μm. Further, impurity concentration in buffer layer 121 is, for example, $5 \times 10^{17}$ cm$^{-3}$. Thickness of breakdown voltage holding layer 122 is, for example, 10 μm. Further, concentration of n type conductive impurity is, for example, $5 \times 10^{15}$ cm$^{-3}$.

Next, photoluminescence of the main surface (upper surface in FIG. 27) of epitaxial substrate 90V is measured substantially in the same manner as in Embodiment 3 (FIG. 26: step S120). If a defective region or regions are removed by the unit of substrate as in Embodiment 3, any defective epitaxial substrate is removed at this stage from the manufacturing process of MOSFET 100. On the other hand, if a defective region or regions are removed as parts of one substrate as in the modification 3 of Embodiment 3, removal from the manufacturing process of epitaxial substrate does not take place here, but the defective regions are removed after the dicing step described later.

Figure 28:
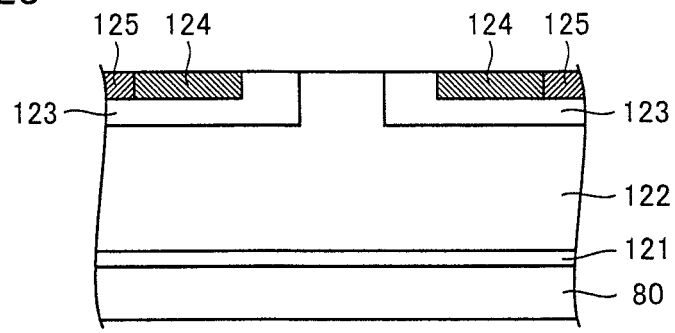
FIG. 28 is a partial cross-sectional view schematically showing the second step of the method of manufacturing the semiconductor device shown in FIG. 25.

As shown in FIG. 28, by the implantation step (FIG. 26: step S130), p region 123, n$^+$ region 124 and p$^+$ region 125 are formed in the following manner.

First, p-type impurity is selectively introduced to a part of breakdown voltage holding layer 122, so that p region 123 is formed. Next, n-type conductive impurity is selectively introduced to a prescribed region to form n$^+$ region 124, and p-type conductive impurity is selectively introduced to a prescribed region to form p$^+$ region 125. Selective introduction of impurities is done using a mask formed, for example, of an oxide film.

Following the implantation step as such, an activation annealing treatment is done. By way of example, annealing is done in an argon atmosphere, at a heating temperature of 1700° C. for 30 minutes.

Figure 29:
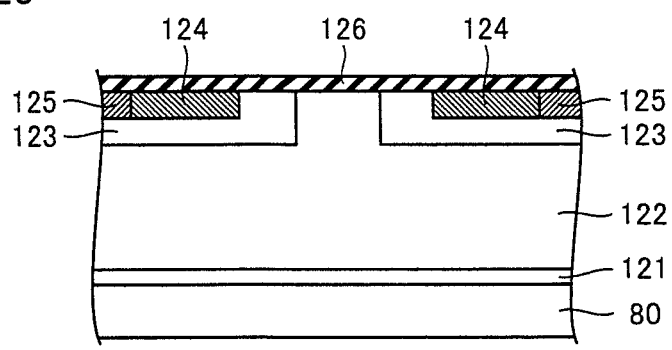
FIG. 29 is a partial cross-sectional view schematically showing the third step of the method of manufacturing the semiconductor device shown in FIG. 25.

As shown in FIG. 29, the gate insulating film forming step (FIG. 26: step S140) is performed. Specifically, oxide film 126 is formed to cover breakdown voltage holding layer 122, p region 123, n$^+$ region 124 and p$^+$ region 125. The film may be formed by dry oxidation (thermal oxidation). Conditions for dry oxidation are, for example, heating temperature of 1200° C. and heating time of 30 minutes.

Thereafter, the nitrogen annealing step (FIG. 26: step S150) is done. Specifically, annealing is done in a nitrogen monoxide (NO) atmosphere. Conditions for this process are, for example, heating temperature of 1100° C. and heating time of 120 minutes. As a result, nitrogen atoms are introduced to the vicinity of interface between oxide film 126 and each of breakdown voltage holding layer 122, p region 123, n$^+$ region 124 and p$^+$ region 125.

Following the annealing step using nitrogen monoxide, annealing using argon (Ar) gas as an inert gas may be performed. Conditions for the process are, for example, heating temperature of 1100° C. and heating time of 60 minutes.

Figure 30:
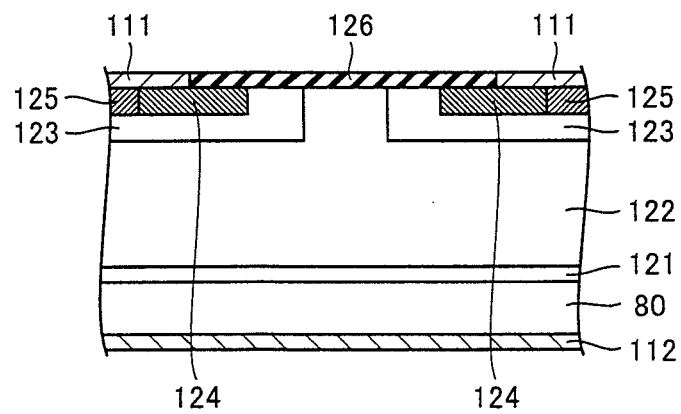
FIG. 30 is a partial cross-sectional view schematically showing the fourth step of the method of manufacturing the semiconductor device shown in FIG. 25.

As shown in FIG. 30, by the electrode forming step (FIG. 26: step S160), source electrode 111 and drain electrode 112 are formed in the following manner.

First, on oxide film 126, using photolithography, a resist film having a pattern is formed. Using the resist film as a mask, portions of oxide film 126 positioned on n$^+$ region 124 and p$^+$ region 125 are removed by etching. Thus, openings are formed in oxide film 126. Next, a conductive film is formed to be in contact with each of n$^+$ region 124 and p$^+$ region 125 in the openings. Then, the resist film is removed, whereby portions of the conductive film that have been positioned on the resist film are removed (lift off). The conductive film may be a metal film and, by way of example, it is formed of nickel (Ni). As a result of this lift off, source electrode 111 is formed.

Here, heat treatment for alloying is preferably carried out. By way of example, heat treatment is done in an atmosphere of argon (Ar) gas as an inert gas, at a heating temperature of 950° C. for 2 minutes.

Again referring to FIG. 25, on source electrode 111, upper source electrode 127 is formed. Further, on oxide film 126, gate electrode 110 is formed. Further, on the backside surface (lower surface in the figure) of single crystal substrate 80, drain electrode 112 is formed.

Next, the dicing step (FIG. 26: step S170) is executed substantially in the similar manner as the dicing along dotted lines LD in Embodiment 3 (FIG. 23). Thus, a plurality of chips are cut out. If the defective regions in one substrate are removed as in the modification of Embodiment 3, chips including defective regions are removed from the plurality of chips.

By the above-described manner, MOSFET 100 (FIG. 25) is obtained.

It is noted that a structure having conductivity types reversed from the structure described above, that is, p-type and n-type reversed, may be used. Further, though a vertical DiMOSFET has been described as an example, other semiconductor devices may be manufactured using the composite substrate in accordance with the present invention. For instance, a RESURF-JFET (Reduced Surface Field-Junction Field Effect Transistor) may be manufactured.

Although the present invention has been described and illustrated in detail, it is clearly understood that the same is by way of illustration and example only and is not to be taken by way of limitation, the scope of the present invention being interpreted by the terms of the appended claims.

What is claimed is:

1. A silicon carbide substrate, comprising:
    a side surface; and
    a main surface surrounded by said side surface; wherein
    said silicon carbide substrate has a hexagonal crystal structure;
    said main surface is inclined by an off angle in an off direction from {0001} plane of said hexagonal crystal; and
    said main surface has such a characteristic that, among the regions emitting photoluminescent light having a wavelength exceeding 650 nm of said main surface caused by excitation light having higher energy than band-gap of the hexagonal silicon carbide, the number of those having a dimension of at most 15 μm in a direction perpendicular to said off direction and a dimension in a direction parallel to said off direction not larger than a value obtained by dividing penetration length of said excitation light in the hexagonal silicon carbide by a tangent of said off angle is at most $1 \times 10^4$ per 1 $cm^2$.

2. The silicon carbide substrate according to claim 1, wherein
    said emitting region is a region emitting photoluminescent light having a wavelength exceeding 750 nm.

3. The silicon carbide substrate according to claim 1, wherein
    said emitting region is a region emitting photoluminescent light having a wavelength exceeding 650 nm and shorter than 950 nm.

4. The silicon carbide substrate according to claim 1, wherein
    said emitting region is a region emitting photoluminescent light having a wavelength exceeding 750 nm and shorter than 950 nm.

5. The silicon carbide substrate according to claim 1, wherein
    said main surface has such a characteristic that the number of said emitting regions is at most $1 \times 10^4$ per 1 $cm^2$.

6. The silicon carbide substrate according to claim 1, comprising a silicon carbide layer having said main surface, and a base substrate supporting said silicon carbide layer, wherein said silicon carbide layer is epitaxially formed on said base substrate.

7. A semiconductor device, comprising the silicon carbide substrate according to claim 1.

8. A method of manufacturing a silicon carbide substrate, comprising the steps of:
    preparing a plurality of silicon carbide single crystals each having a main surface and a crystal structure of hexagonal crystal; and
    measuring photoluminescence of said main surface of each of said plurality of silicon carbide single crystals; wherein
    said step of measuring photoluminescence includes the step of irradiating said main surface with excitation light having higher energy than band-gap of the hexagonal silicon carbide, and the step of observing emitting regions of photoluminescent light having a wavelength exceeding 650 nm caused by said excitation light;
    said method further comprising the step of
    attaining crystal growth of silicon carbide through sublimation method, using as a seed crystal one of said plurality of silicon carbide single crystals of which number of said emitting regions per unit area is smaller than a prescribed number.

9. The method of manufacturing a silicon carbide substrate according to claim 8, wherein
    said emitting region is a region emitting photoluminescent light having a wavelength exceeding 750 nm.

10. The method of manufacturing a silicon carbide substrate according to claim 8, wherein
    said emitting region is a region emitting photoluminescent light having a wavelength exceeding 650 nm and shorter than 950 nm.

11. The method of manufacturing a silicon carbide substrate according to claim 8, wherein
    said emitting region is a region emitting photoluminescent light having a wavelength exceeding 750 nm and shorter than 950 nm.

12. A method of manufacturing a semiconductor device, comprising the steps of:
    preparing a plurality of silicon carbide substrates each having a main surface and a crystal structure of hexagonal crystal; and
    measuring photoluminescence of said main surface of each of said plurality of silicon carbide substrates; wherein
    said step of measuring photoluminescence includes the step of irradiating said main surface with excitation light having higher energy than band-gap of the hexagonal silicon carbide, and the step of observing emitting regions of photoluminescent light having a wavelength exceeding 650 nm caused by said excitation light;
    said method further comprising the step of
    removing a defective region having the number of said emitting regions per unit area on said main surface larger than a prescribed number, from a product fabricating region as a region for fabricating said semiconductor device.

13. The method of manufacturing a semiconductor device according to claim 12, wherein
    said emitting region is a region emitting photoluminescent light having a wavelength exceeding 750 nm.

14. The method of manufacturing a semiconductor device according to claim 12, wherein
    said emitting region is a region emitting photoluminescent light having a wavelength exceeding 650 nm and shorter than 950 nm.

15. The method of manufacturing a semiconductor device according to claim 12, wherein
said emitting region is a region emitting photoluminescent light having a wavelength exceeding 750 nm and shorter than 950 nm.

16. The method of manufacturing a semiconductor device according to claim 12, wherein
said step of removing includes the step of removing the silicon carbide substrate having said defective region from manufacturing process of said semiconductor device.

17. The method of manufacturing a semiconductor device according to claim 12, wherein
said step of removing includes the step of removing said defective region of the silicon carbide substrate having said defective region from manufacturing process of said semiconductor device, and determining a region other than said defective region as said product fabricating region.

* * * * *